United States Patent [19]

Carter et al.

[11] Patent Number: 5,371,008
[45] Date of Patent: Dec. 6, 1994

[54] SUBSTRATE ASSISTED CATALYSIS

[75] Inventors: Paul J. Carter, San Francisco; James A. Wells, Burlingame, both of Calif.

[73] Assignee: Genencor International, Inc., South San Francisco, Calif.

[21] Appl. No.: 90,472

[22] Filed: Jul. 12, 1993

Related U.S. Application Data

[60] Continuation of Ser. No. 909,999, Jul. 7, 1992, abandoned, and a continuation-in-part of Ser. No. 35,652, Apr. 6, 1987, abandoned, which is a continuation-in-part of Ser. No. 858,594, Apr. 30, 1986, abandoned, said Ser. No. 909,999, is a division of Ser. No. 823,039, Jan. 14, 1992, abandoned, which is a continuation of Ser. No. 334,081, Apr. 4, 1989, which is a continuation-in-part of Ser. No. 127,134, Dec. 1, 1987, abandoned, which is a continuation-in-part of Ser. No. 846,627, Apr. 1, 1986, abandoned, which is a continuation-in-part of Ser. No. 614,615, May 29, 1984, abandoned, and a continuation-in-part of Ser. No. 858,594, Apr. 30, 1986, abandoned, which is a continuation-in-part of Ser. No. 614,612, May 29, 1984, Pat. No. 4,760,025, Ser. No. 614,615, May 29, 1984, abandoned, Ser. No. 614,617, May 29, 1984, abandoned, and Ser. No. 614,491, May 29, 1984, abandoned.

[51] Int. Cl.$^5$ .......................... C12N 9/56; C12N 9/54
[52] U.S. Cl. .................................... 435/222; 435/221; 530/350
[58] Field of Search ................ 435/222, 221, 183; 530/350

[56] References Cited

U.S. PATENT DOCUMENTS

| | | | |
|---|---|---|---|
| 4,543,329 | 9/1985 | Daum et al. | 435/69 |
| 4,760,025 | 7/1988 | Estell et al. | 435/222 |

OTHER PUBLICATIONS

Estell, D. A., et al, (1986) Science 233, 659–663.
Wells, J. A., et al. (1987) Proc. Natl. Acad. Sci. USA 84, 1219–1223.
Wells, J. A. et al., (1987) Proc. Natl. Acad. Sci. USA, 84, 5167–5171.
Wells, et al., "Nucleic Acids Research", (1983) vol. 11, pp. 7911–7923.
Stauffer et al., "The Journal of Biological Chemistry", (1969) vol. 244, pp. 5333–5338.
Polgar, et al., "Biochimica et Biophysica Acta", (1981) 667, pp. 351–354.
Thomas, et al., "Nature", (1985) vol. 318, pp. 37–38.
Gardell, et al., "Nature", (1985) vol. 317, pp. 551–555.
Vasantha, et al., "Journal of Bacteriology", (1986) vol. 165, pp. 837–842.
Zaghloul, et al., "Journal of Bacteriology", (1985) Nov. vol. 164 pp. 550–555.
Carter, et al., "Science", (1987) vol. 237, pp. 394–399.
Wells, et al., Cold Spring Harbor Symposia on Quantitative Biology, (1987), vol. LII, pp. 647–652.
Winter, et al., "Nature", (1982) vol. 299, pp. 756–758.
Toney et al., "Science", (1989) vol. 243, pp. 1485–1488.
Iverson, et al., "Science", (1989) vol. 243, pp. 1184–1188.

*Primary Examiner*—Charles L. Patterson, Jr.
*Attorney, Agent, or Firm*—Flehr, Hohbach, Test, Albritton & Herbert

[57] ABSTRACT

Novel enzyme mutants are disclosed which are derived from a precursor enzyme by replacing or modifying at least one catalytic functional group of an amino acid residue in a precursor enzyme. Such mutant enzymes have a catalytic preference for substrates which provide the replaced or modified catalytic group or its equivalent such that the substrate together with the enzyme mutant assists in its own catalysis.

12 Claims, 21 Drawing Sheets

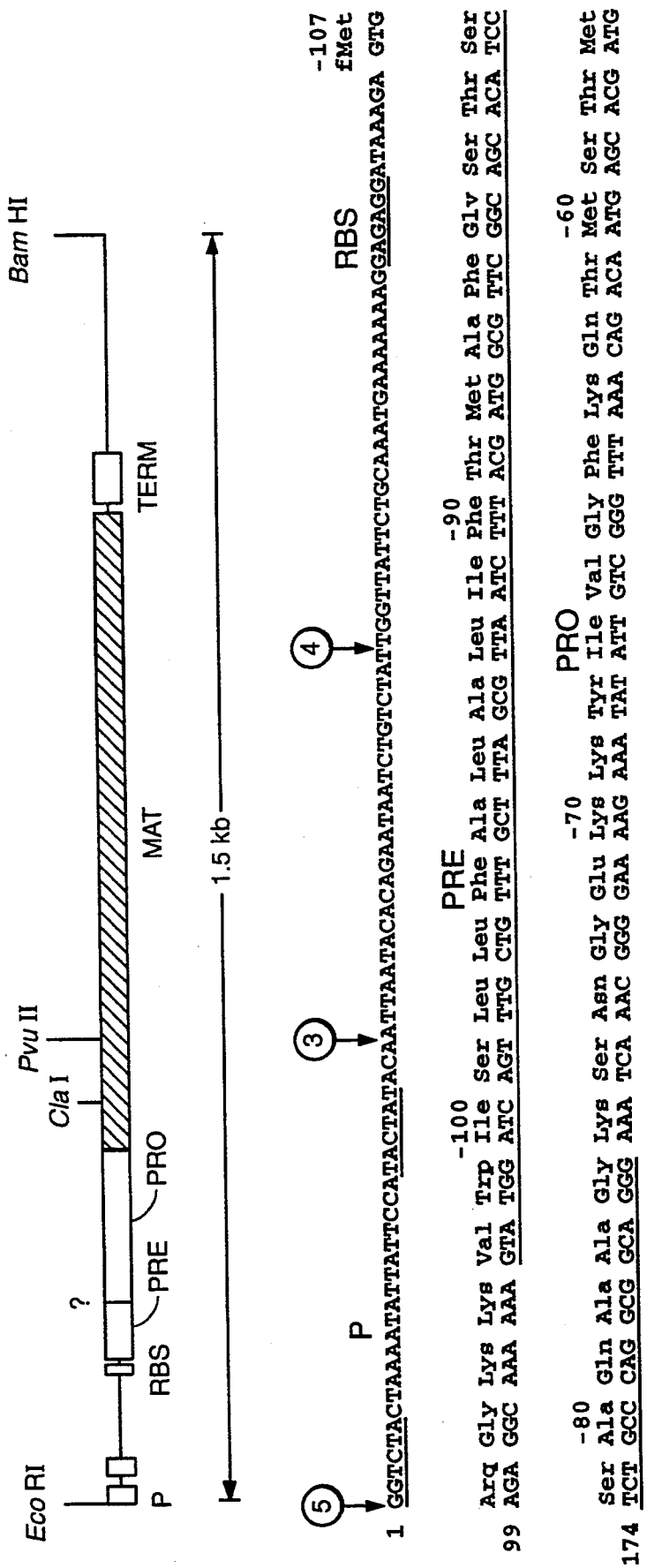

```
                                                      -50                                     -40
249 Ser Ala Ala Lys Lys Lys Asp Val Ile Ser Glu Lys Gly Gly Lys Val Gln Phe Lys Tyr Val Asp Ala
    AGC GCC GCT AAG AAG AAA GAT GTC ATT TCT GAA AAA GGC GGG AAA GTG CAA TTC AAA TAT GTA GAC GCA

-30                                                   -20                                              -10
324 Ala Ser Ala Thr Leu Asn Glu Lys Leu Lys Lys Lys Leu Glu Leu Lys Asp Pro Ser Val Ala Tyr Val Glu Asp
    GCT TCA GCT ACA TTA AAC GAA AAA GCT GTA AAA TTG AAA GAA GAC CCG AGC GTC GCT TAC GTT GAA GAT

-1  1                                                10
399 His Val Ala His Ala Tyr Ala Gln Ser Val Pro Tyr Gly Val Ser Gln Ile Lys Ala Pro Ala Leu His Ser Gln
    CAC GTA GCA CAT GCG TAC GCG CAG TCC GTG CCT TAC GGC GTA TCA CAA ATT AAA GCC CCT GCT CTG CAC TCT CAA
                            ↑MAT 20                                                      30                                        40
474 Gly Tyr Thr Gly Ser Asn Val Lys Val Ala Val Ile Asp Ser Gly Ile Asp Ser Ser His Pro Asn Leu Lys Val
    GGC TAC ACT GGA TCA AAT GTT AAA GTA GCG GTT ATC GAC AGC GGT ATC GAT TCT TCT CAT CCT AAT TTA AAG GTA

Pro Asn                                 60 Asp
549 Ala Gly Gly Ala Ser Met Val Pro Ser Glu Thr Asn Pro Phe Gln Asp Asn Asn Ser His Gly Thr His Val Ala
    GCA GGC GGA GCC AGC ATG GTT CCT TCT GAA ACA AAT CCT TTC CAA GAC AAC AAC TCT CAC GGA ACT CAC GTT GCC

Ser Ala  90
624 Gly Thr Val Ala Ala Leu Asn Asn Ser Ile Gly Val Leu Gly Val Ala Pro Ser Ala Ser Leu Tyr Ala Val Lys
    GGT ACA GTT GCG GCT CTT AAT AAC TCA ATC GGT GTT TTA GGC GTT GCG CCA AGC GCA TCA CTT TAC GCT GTA AAA

Asp Ala 100                                        110
699 Val Leu Gly Ala Asp Gly Ser Gly Gln Tyr Ser Trp Ile Ile Asn Gly Ile Glu Trp Ala Ile Ala Asn Asn Met
    GTT CTC GGT GCT GAC GGT TCC GGC CAA TAC AGC TGG ATT ATT AAC GGA ATC GAG TGG GCG ATC GCA AAC AAT ATG 120                                            130                                            140
774 Asp Val Ile Asn Met Ser Leu Gly Gly Pro Gly Ser Ala Ala Leu Lys Ala Ala Val Asp Lys Ala Val Ala
    GAC GTT ATT AAC ATG AGC CTC GGC GGA CCT GGT TCT GCT GCT TTA AAA GCG GCA GTT GAT AAA GCC GTT GCA
```

*FIG. 1B*

```
                     150                      Ser Thr 160
    Ser Gly Val Val Val Ala Ala Gly Asn Glu Gly Thr Ser Ser Ser Val Gly Tyr Pro Gly
849 TCC GGC GTA GTC GTT GCA GCC GGT AAC GAA GGC ACT TCC AGC TCA GTG GGC TAC CCT GGT 170                      180
    Lys Tyr Pro Ser Val Ile Ala Val Ala Val Asp Ser Asn Gln Arn Ala Ser Phe Ser Ser Val Gly Pro
924 AAA TAC CCT TCT GTC ATT GCA GTA GCT GAC AGC AAC CAA AGA GCA TCT TTC TCA AGC GTA GGA CCT 200                      210
    Glu Leu Asp Val Met Ala Pro Gly Val Ser Ile Gln Ser Thr Leu Pro Gly Asn Lys Tyr Gly Ala Tyr Asn Gly
999 GAG CTT GAT GTC ATG GCA CCT GGC GTA TCT ATC CAA AGC ACG CTT CCT GGA AAC AAA TAC GGC GCG TAC AAC GGT 220                      230                      240
    Thr Ser Met Ala Ser Pro His Val Ala Gly Ala Ala Leu Ile Leu Ser Lys His Pro Asn Trp Thr Asn Thr
1074 ACG TCA ATG GCA TCT CCG CAC GTT GCC GGA GCT GCT TTG ATT CTT TCT AAG CAC CCG AAC TGG ACA AAC ACT

250 Gln                      260
    Gln Val Arg Ser Ser Ser Leu Glu Asn Thr Thr Lys Leu Gly Asp Ser Phe Tyr Tyr Gly Lys Gly Leu Ile Asn
1149 CAA GTC CGC AGC AGT TTA GAA AAC ACC ACT AAA CTT GGT GAT TCT TTC TAC TAT GGA AAA GGG CTG ATC AAC 270                  275
    Val Gln Ala Ala Ala Gln Gln DC
1224 GTA CAG GCA GCG GCT CAG TAA AACATAAAAAACGGGCTTGGCCCCGCGGTTTTTATTATTTTTCTTCCTCCGCATGTTCAATCCGCT

1314 CCATAATCGACGGATGGCTCCCTCTGAAAATTTTAACGAGAAACGGCGGGTTGACCCGGCTCAGTCCCGTAACGGCCAAGTCCTGAAACGTCTCAATCGC

1414 CGCTTCCCGGTTTCCGGTCAGCTCAATGCCGTAACGGTCGGCGGCGTTTCCTGATACCGGGAGACGGCATTCGTAATCGGATC
```

*FIG._1C*

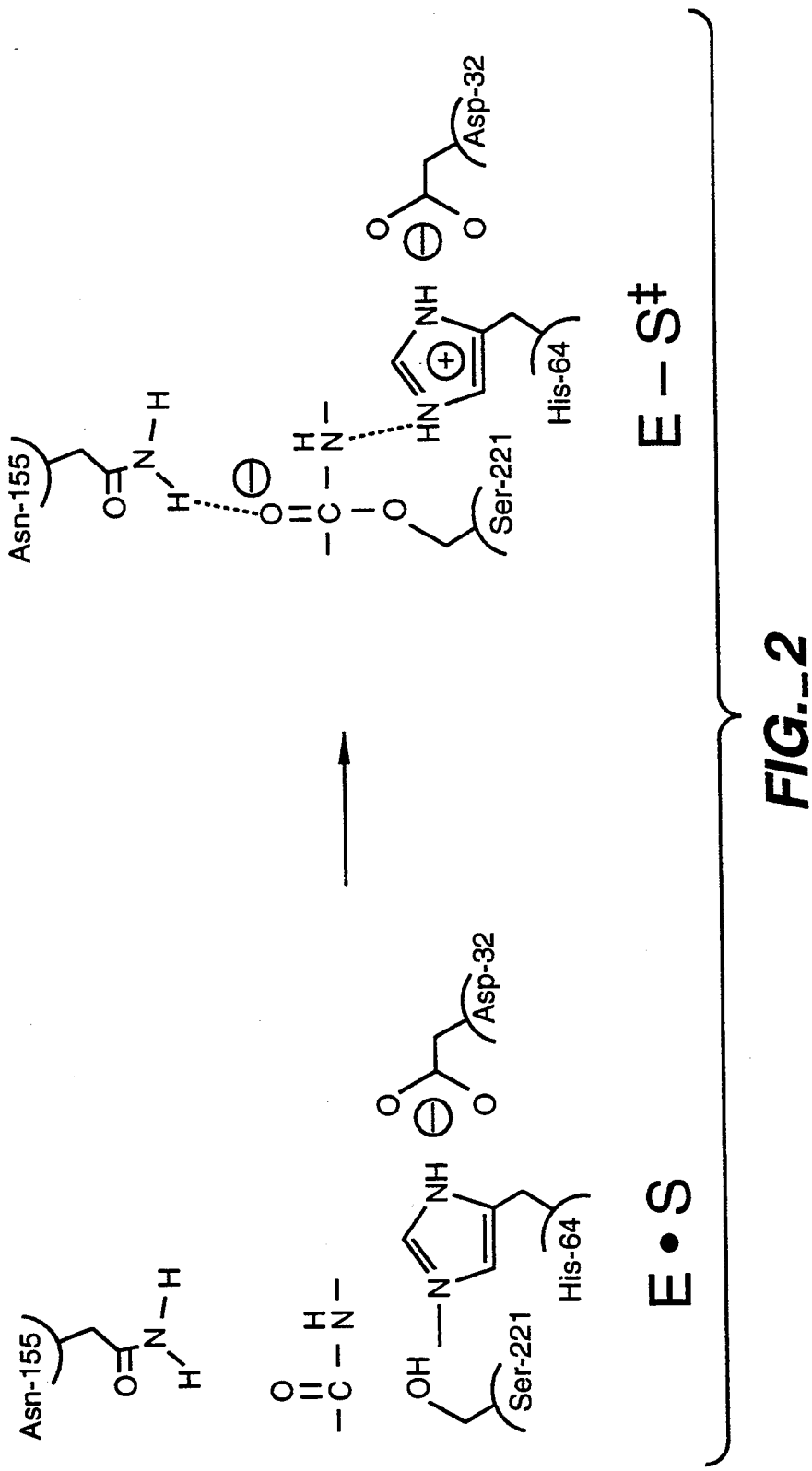
FIG._2

Homology of Bacillus proteases

1. Bacillus amyloliquifaciens
2. Bacillus subtilis var.I168
3. Bacillus licheniformis (carlsbergensis)

ALIGNMENT OF B.AMYLOLIQUIFACIENS SUBTILISIN AND THERMITASE
1. B.amyloliquifaciens subtilisin
2. thermitase

TOTALLY CONSERVED RESIDUES IN SUBTILISINS

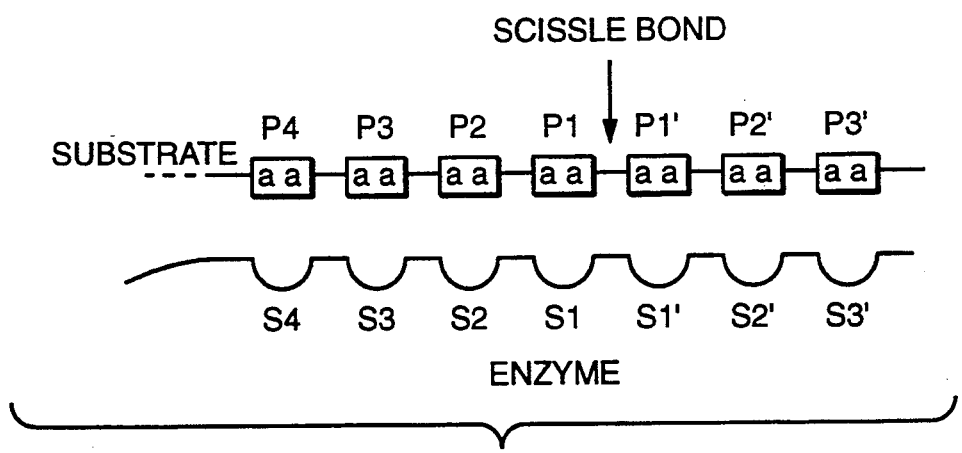
FIG._4
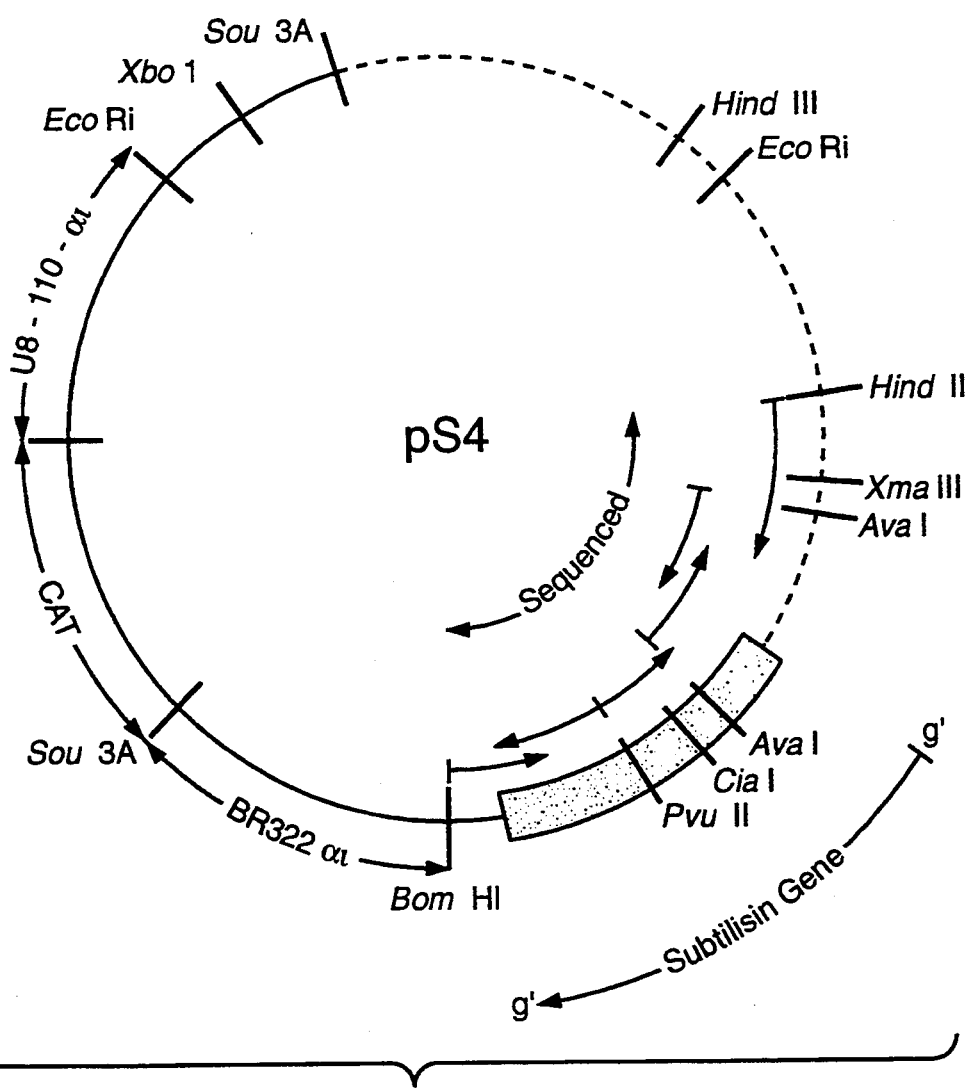
FIG._6

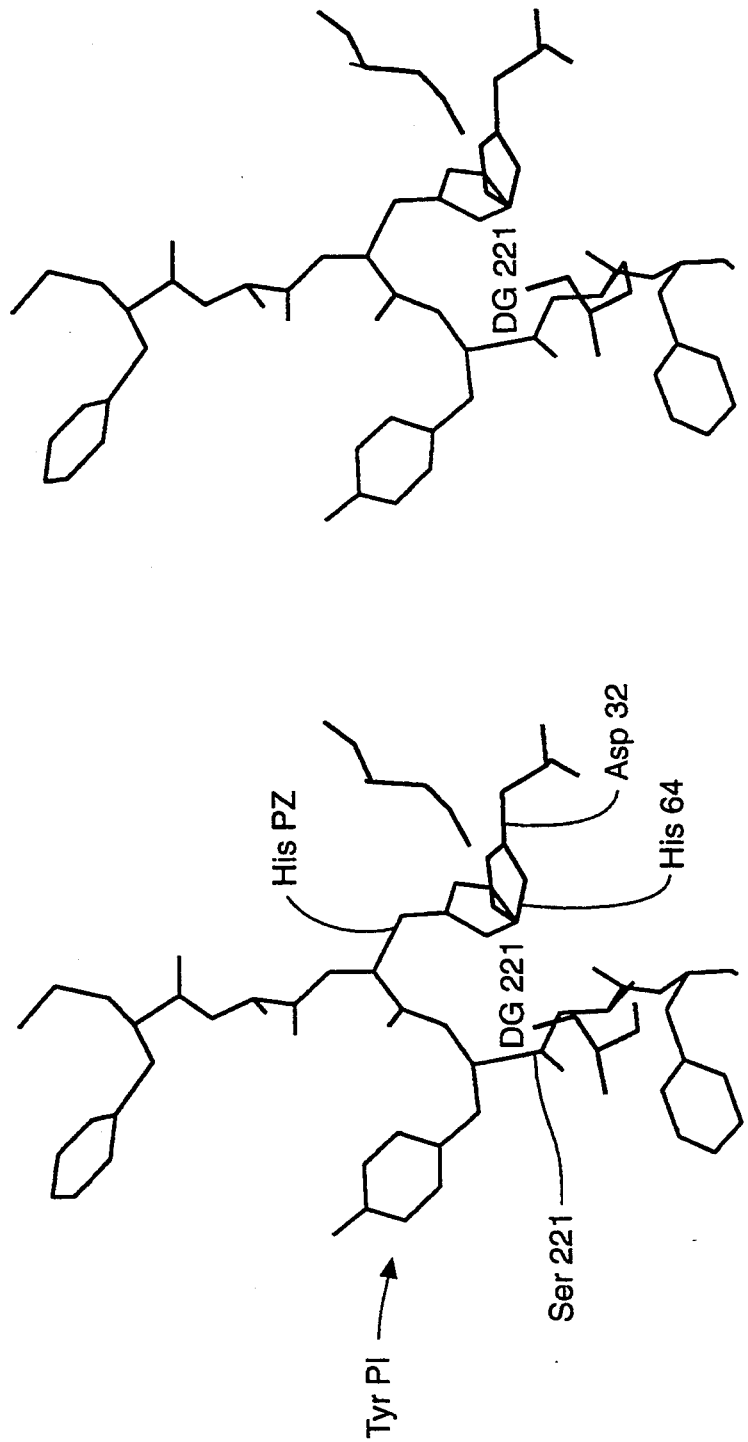
FIG._5

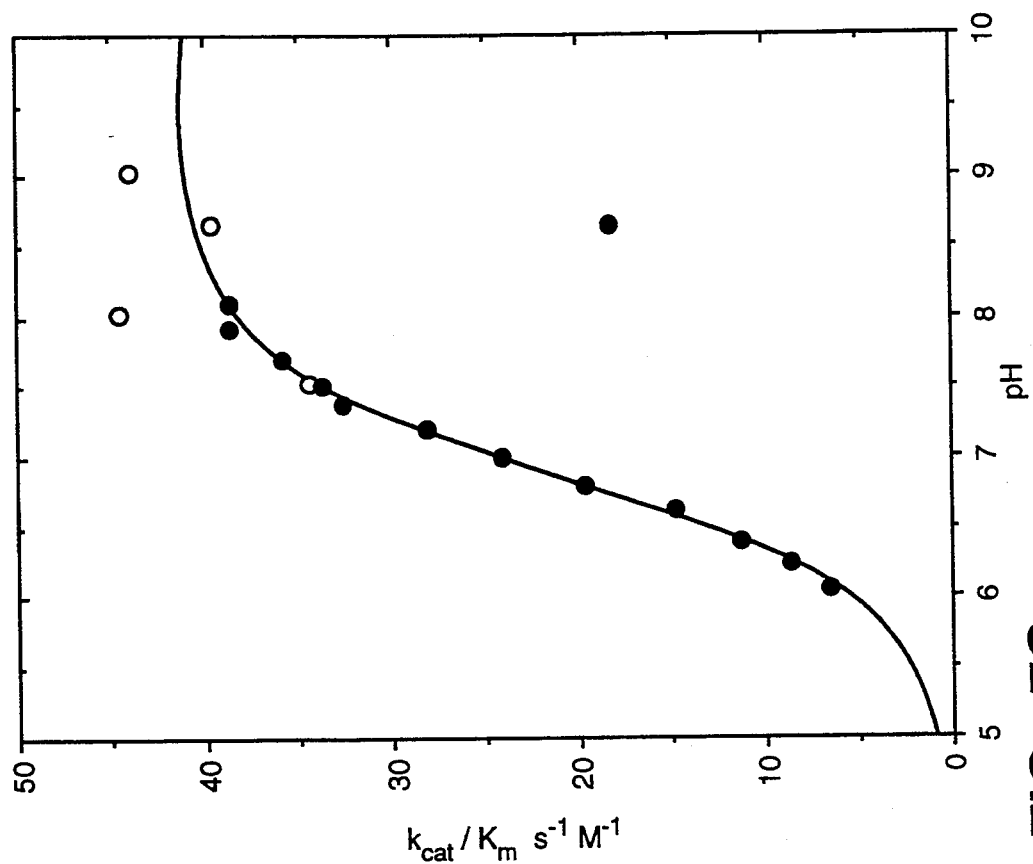
FIG._7C
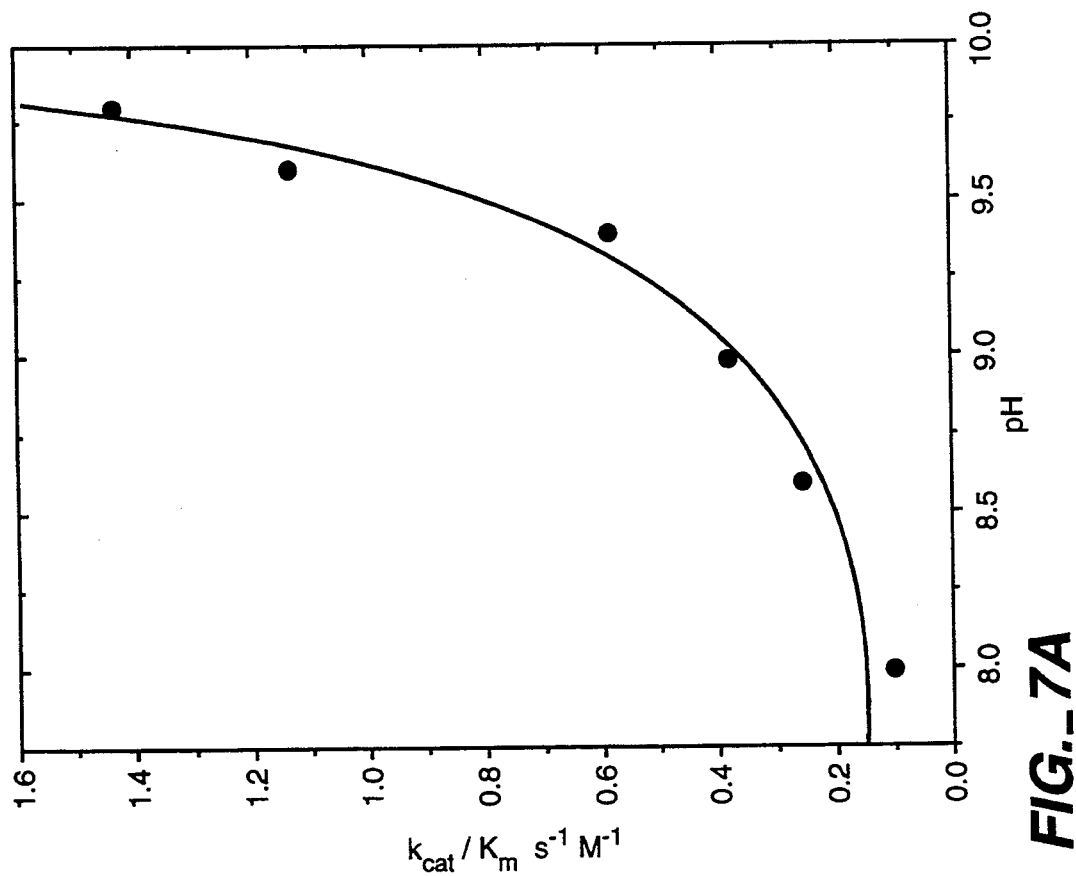
FIG._7A

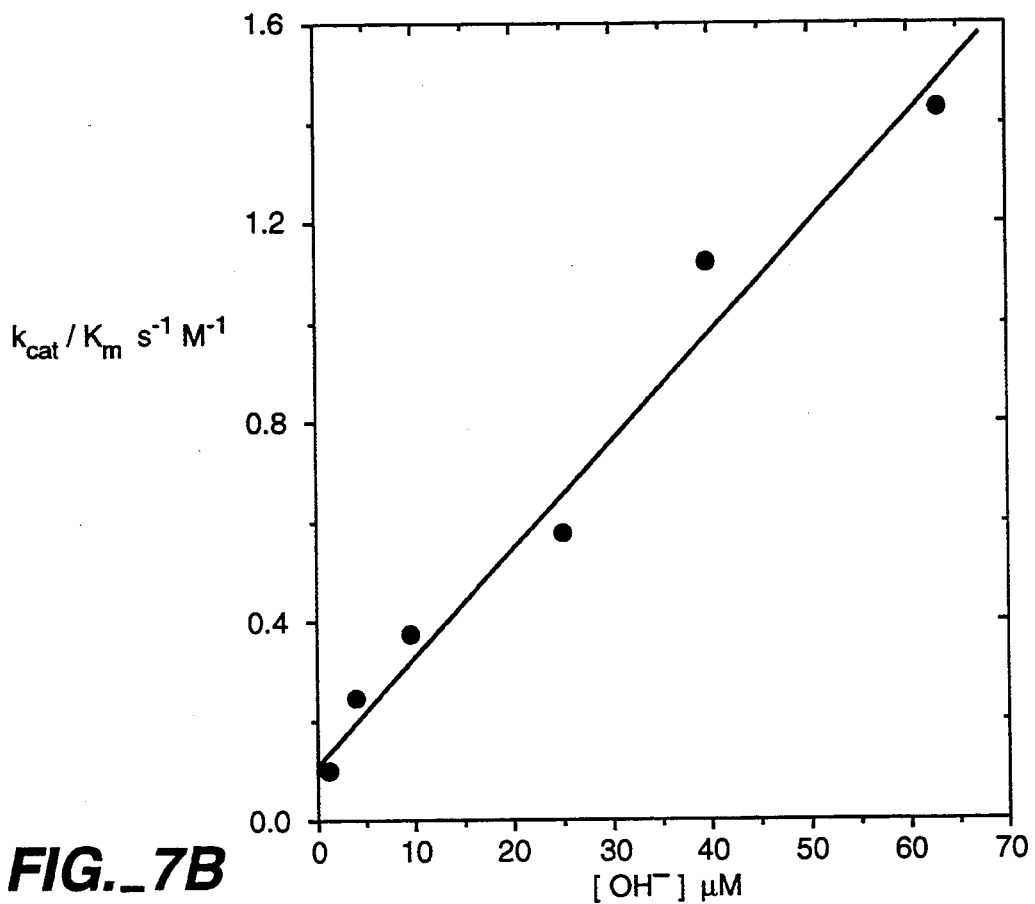
FIG._7B
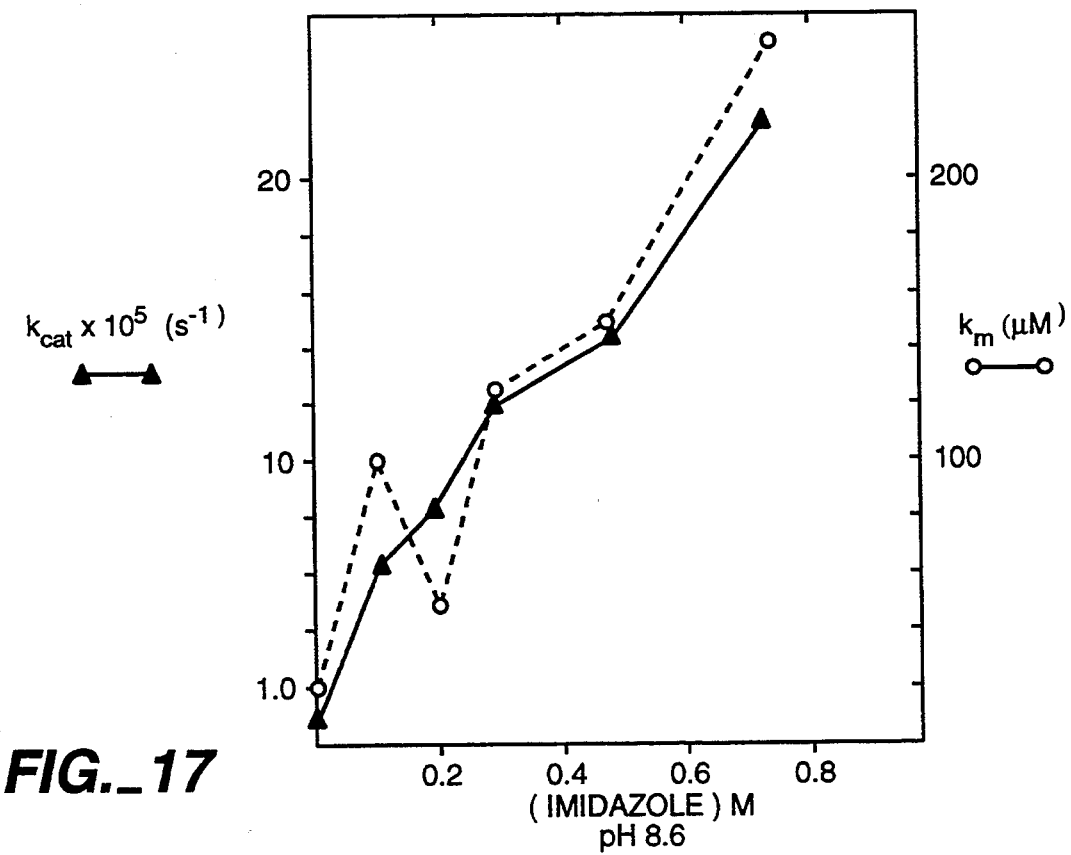
FIG._17

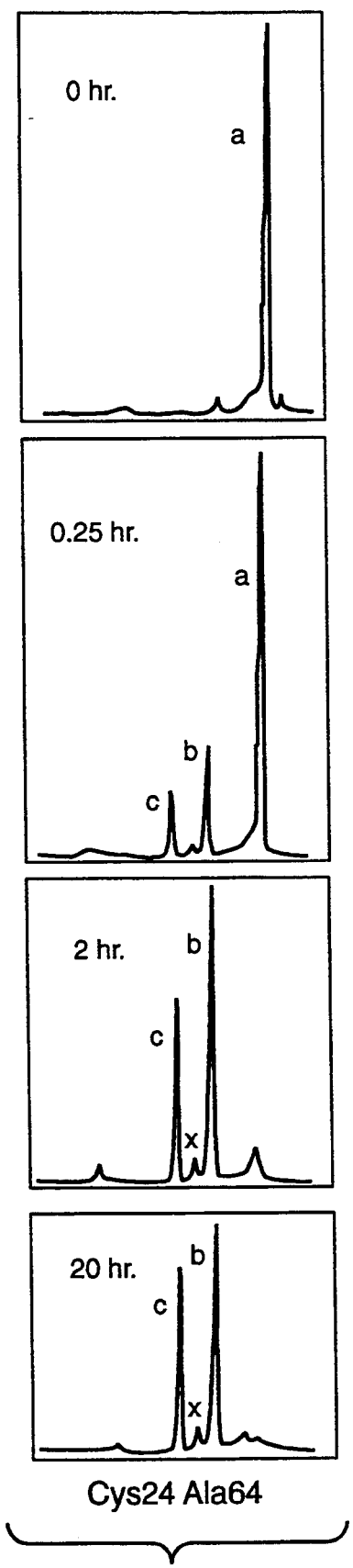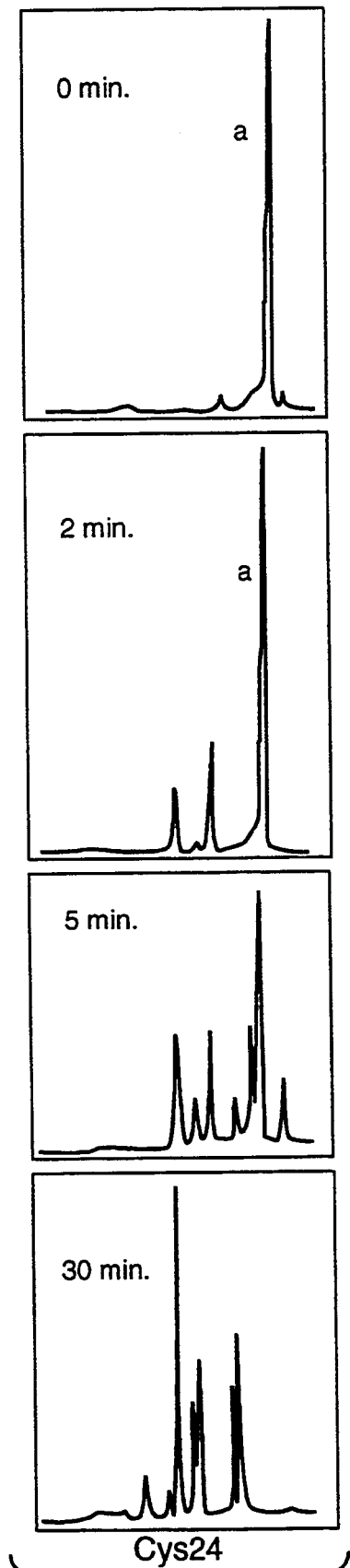
FIG._8A    FIG._8B

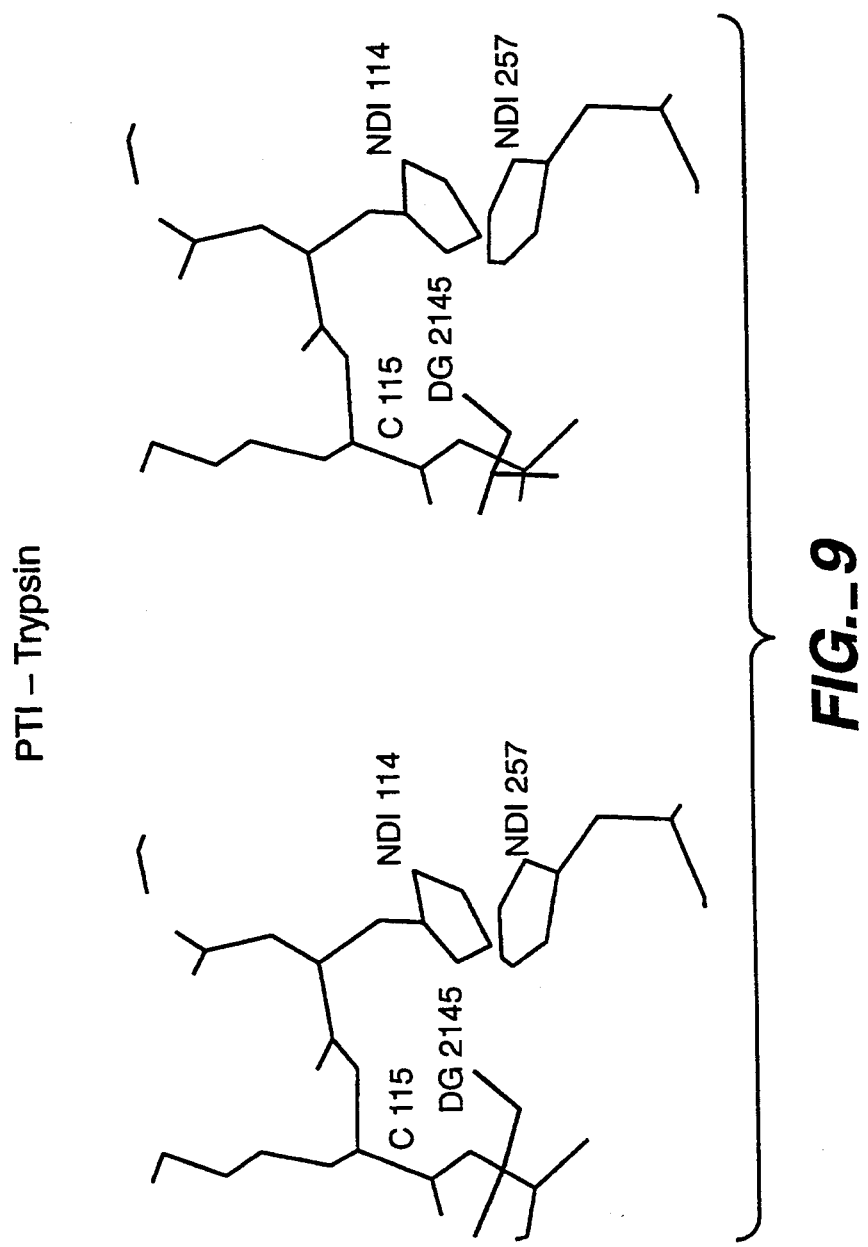
FIG._9

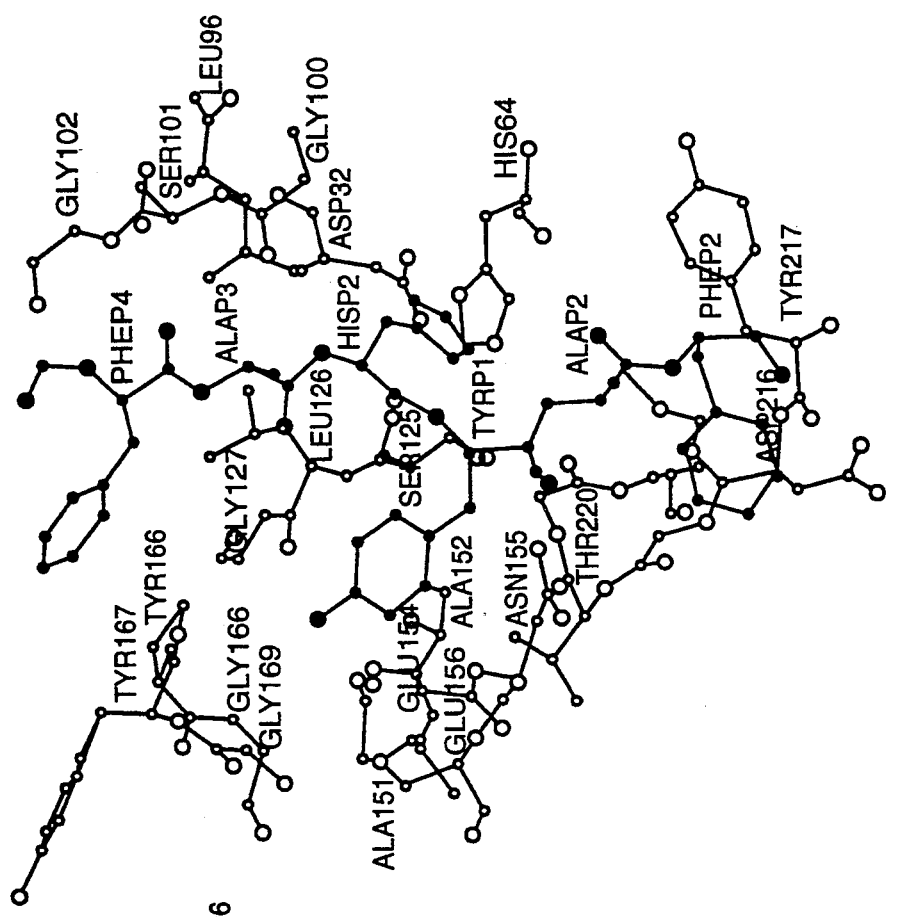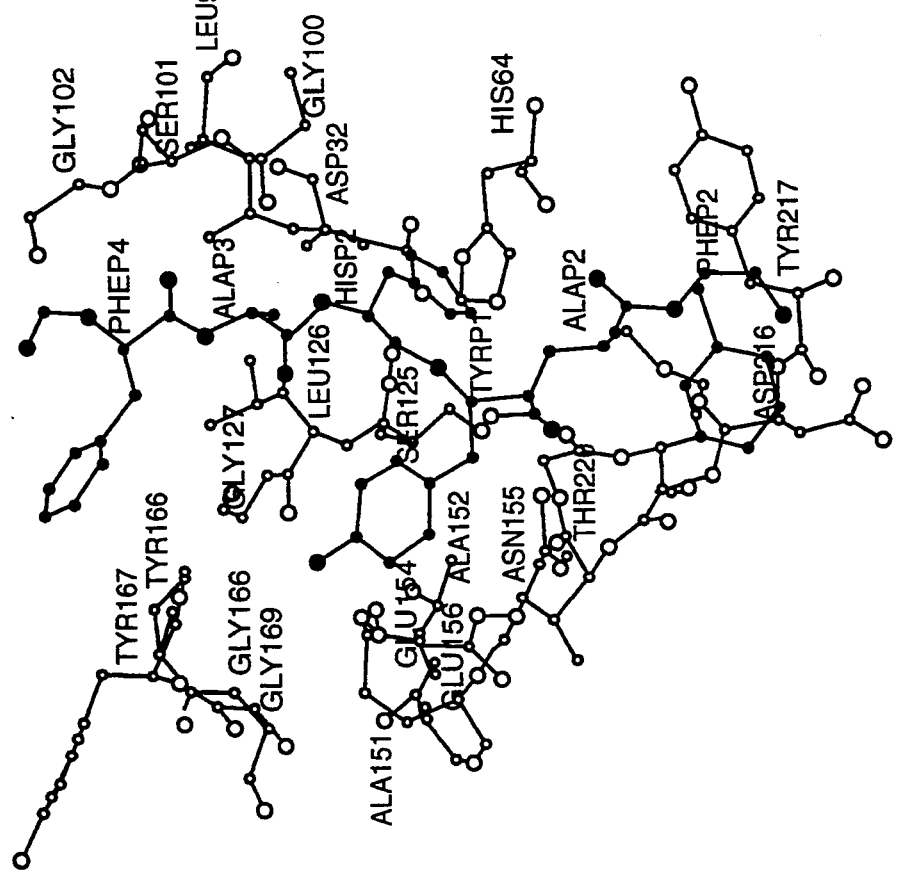
FIG._10

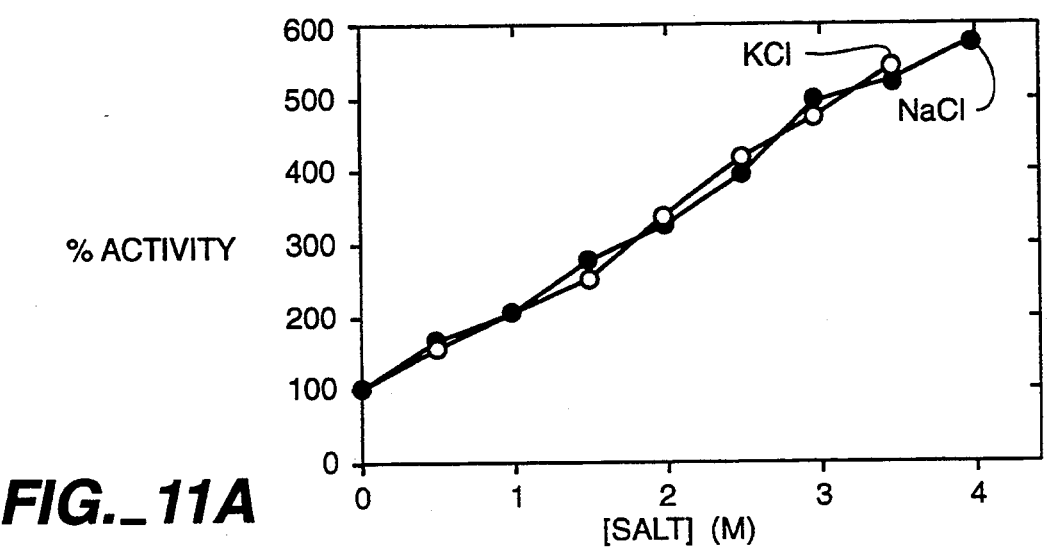
FIG._11A
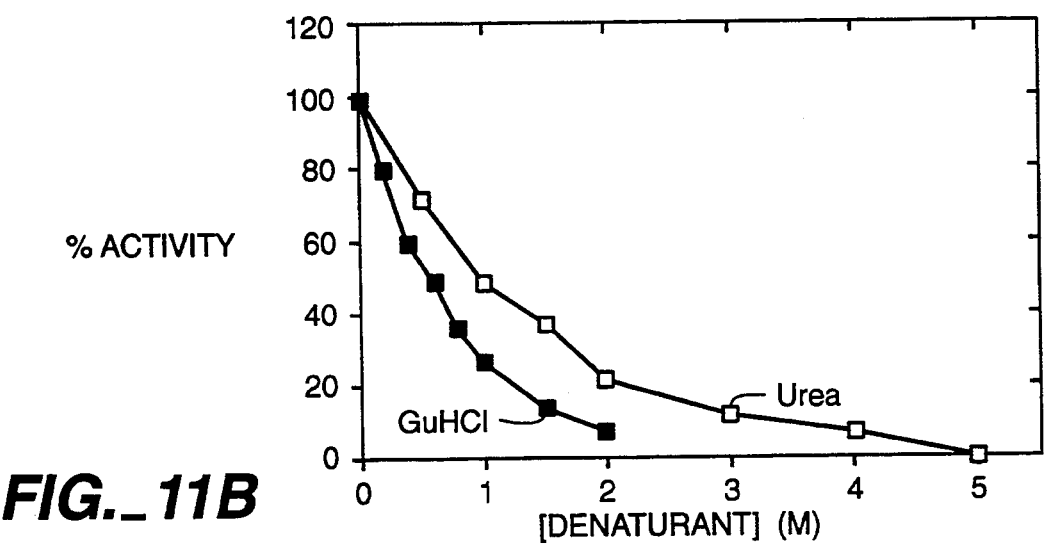
FIG._11B
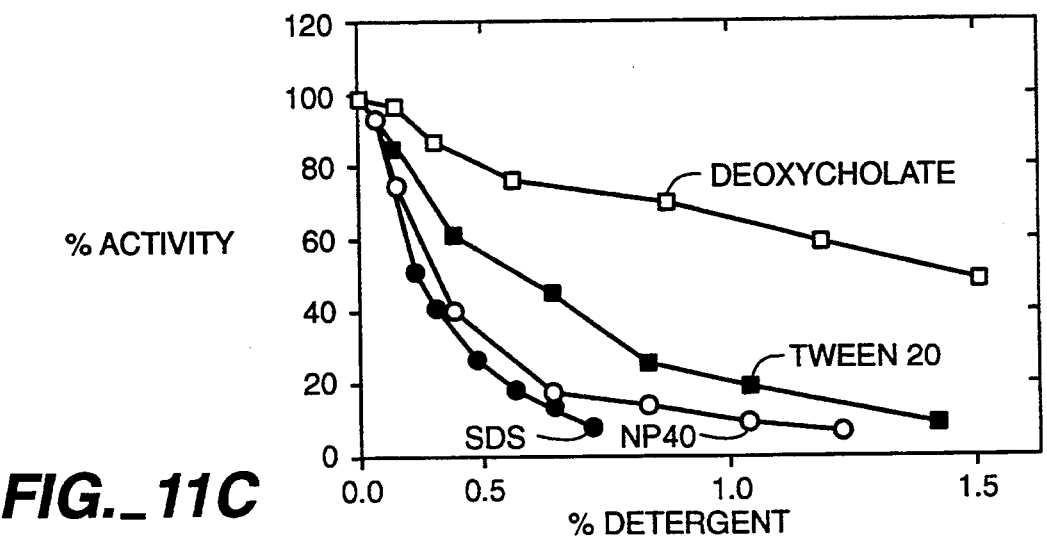
FIG._11C

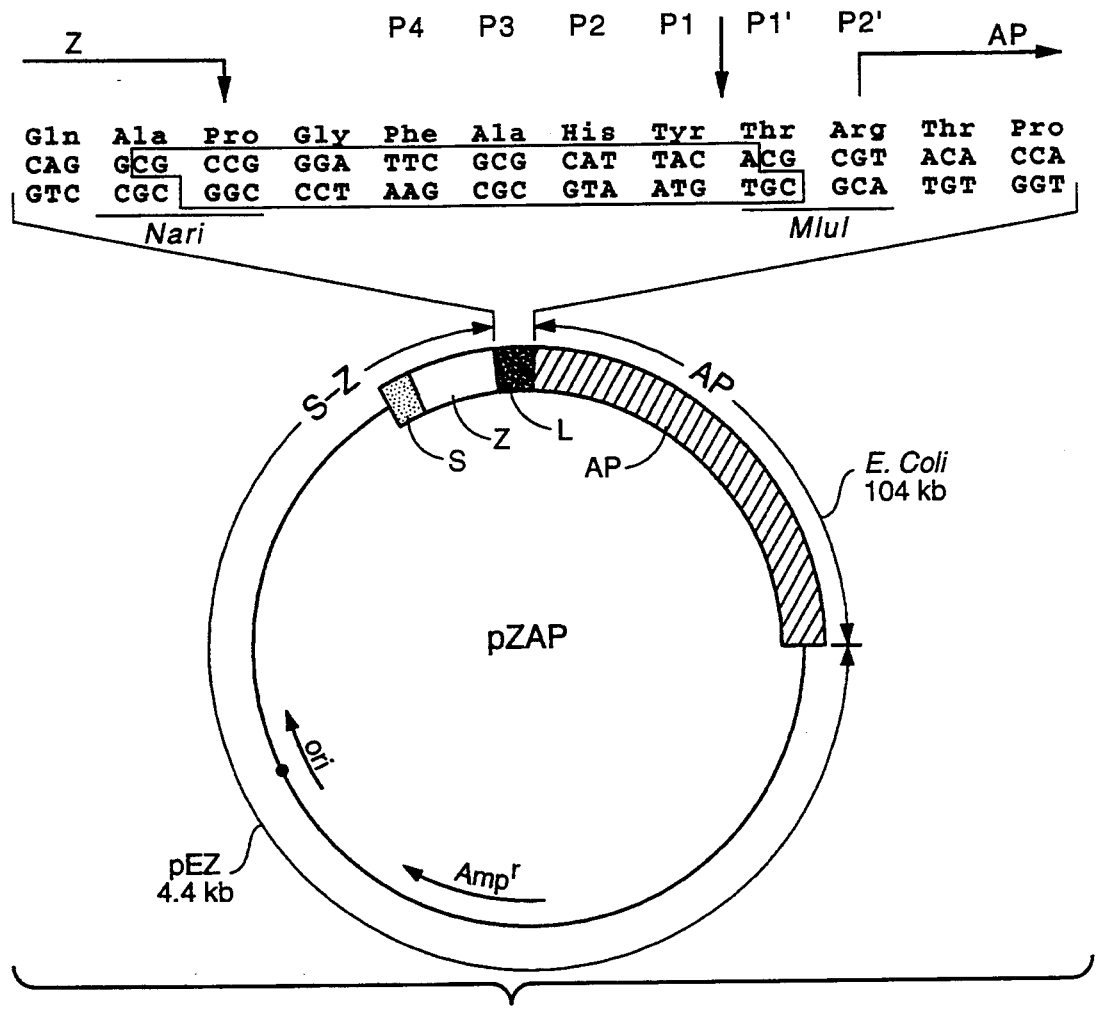
FIG._12
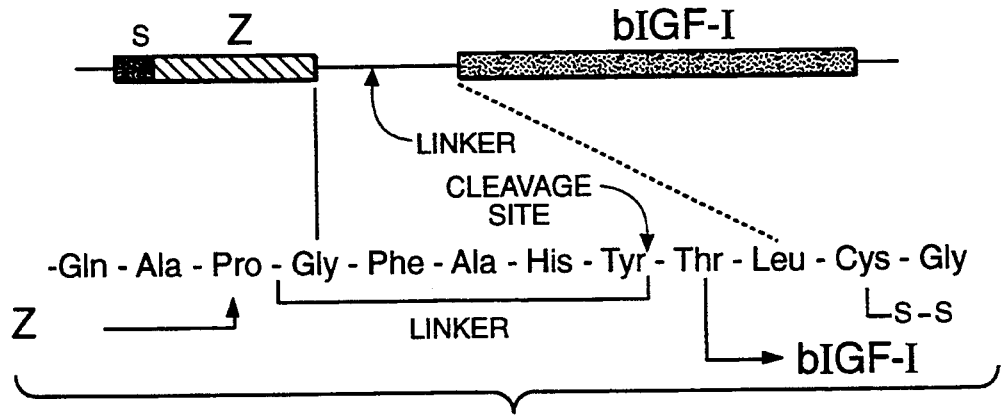
FIG._14

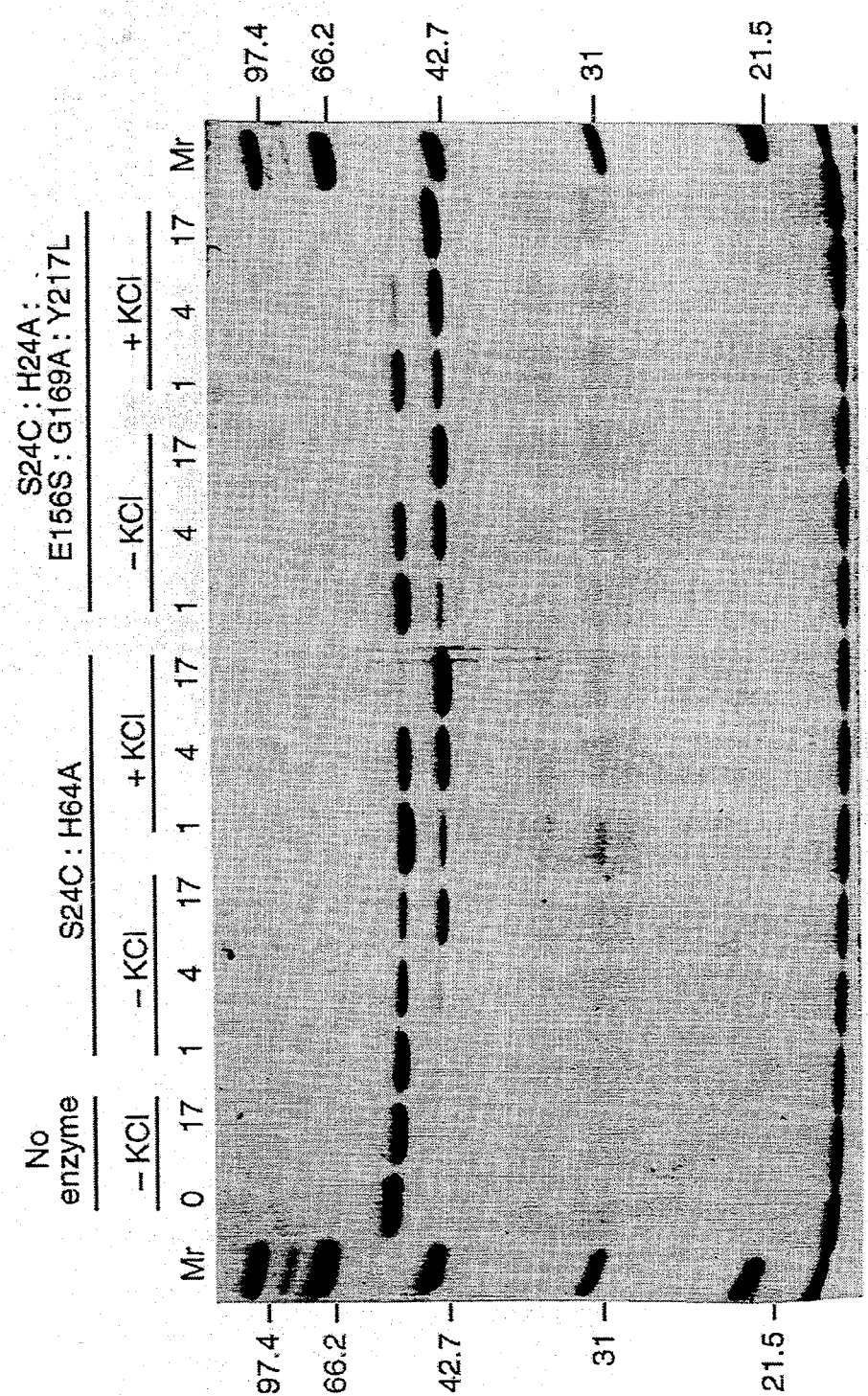
FIG._13

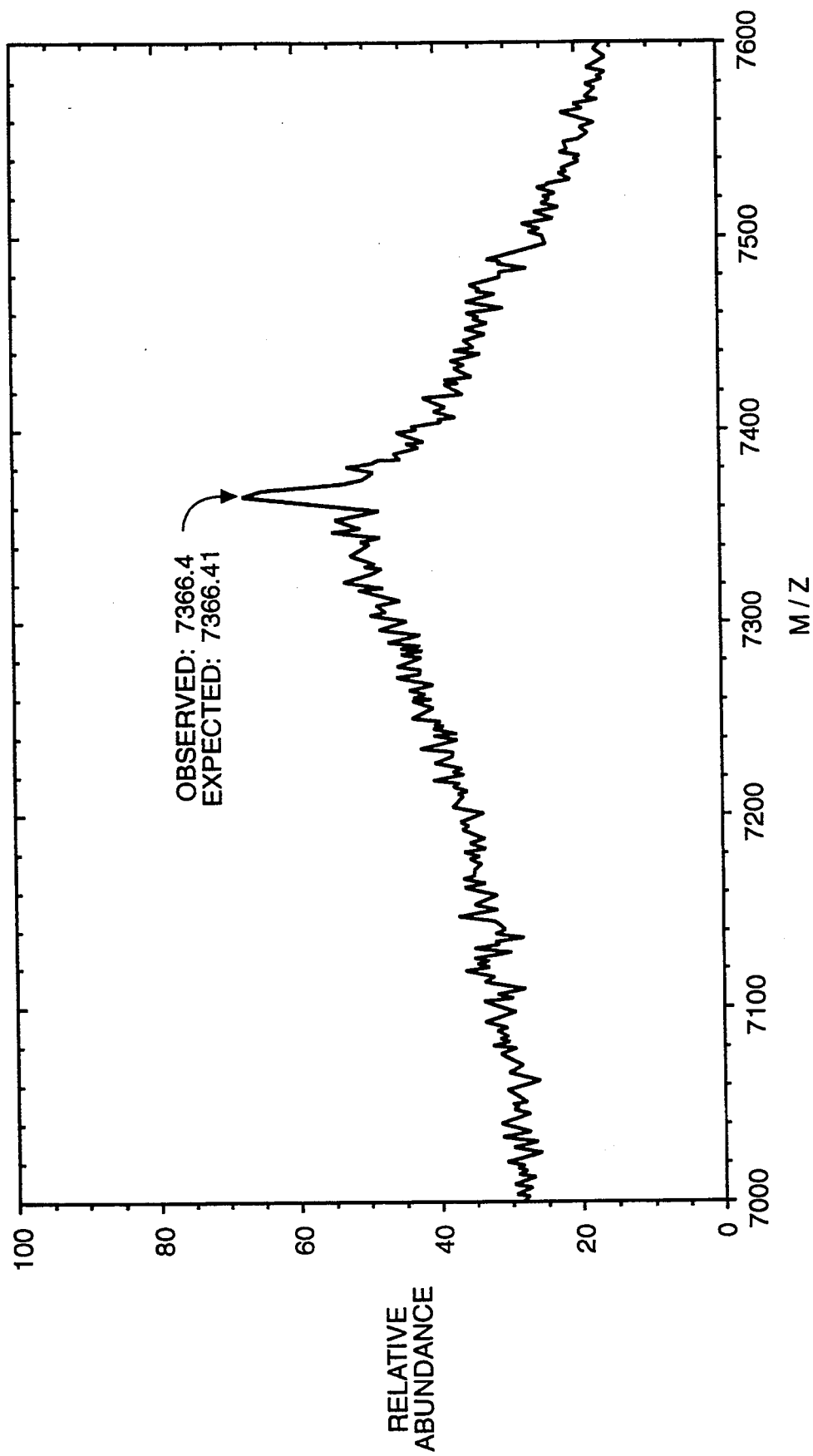
FIG._15

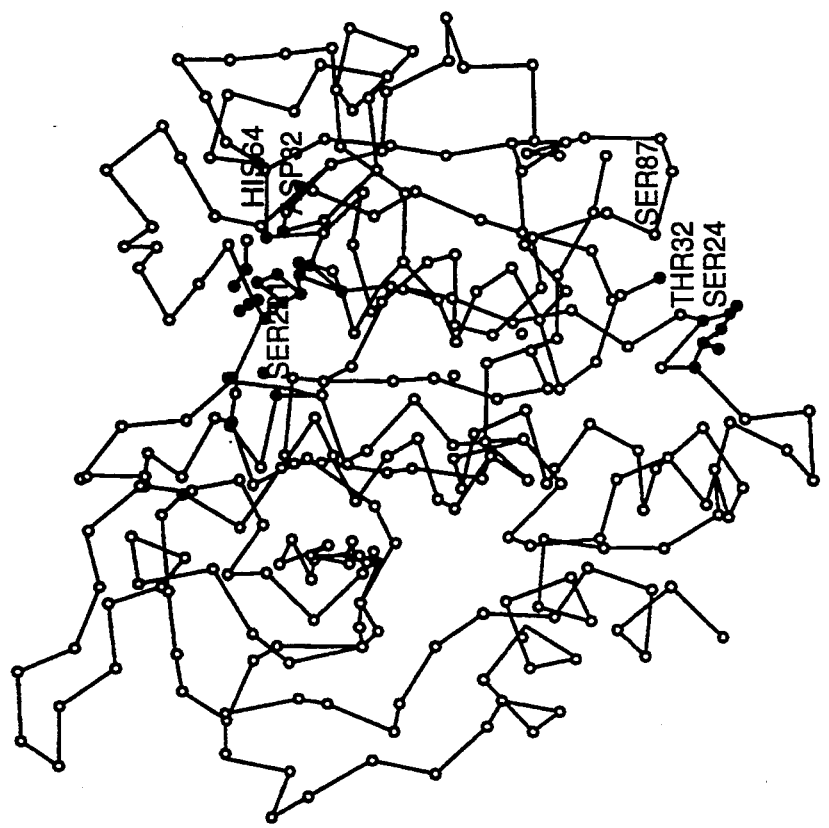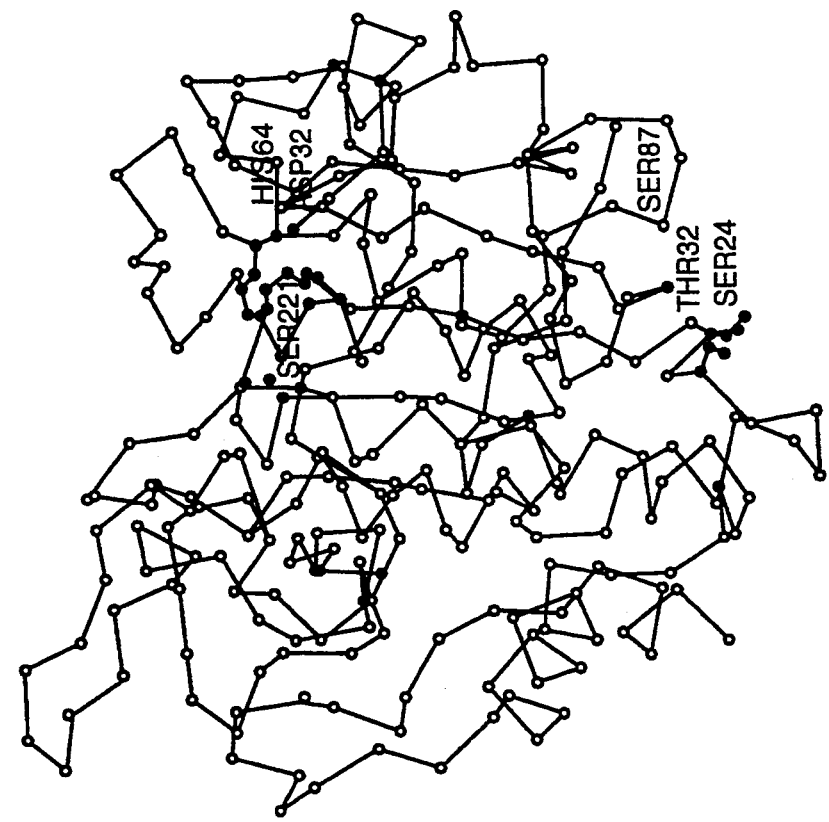
FIG._16

SUBSTRATE ASSISTED CATALYSIS

This is a continuation of U.S. patent application Ser. No. 909,999 filed Jul. 7, 1992 now abandoned, which is a division of U.S. patent application Ser. No. 823,039 filed Jan. 14, 1992, now abandoned, which is a continuation of U.S. patent application Ser. No. 334,081 filed Apr. 4, 1989, which is a continuation-in-part of U.S. patent application Ser. No. 127,134 filed Dec. 1, 1987, now abandoned, which is a continuation-in-part of U.S. patent application Ser. No. 846,627 filed Apr. 1, 1986, now abandoned, which is a continuation-in-part of U.S. patent application Ser. No. 614,615 filed May 29, 1984, now abandoned, and U.S. patent application Ser. No. 858,594 filed Apr. 30, 1986, now abandoned, which is a continuation-in-part of U.S. patent application Ser. Nos. 614,612, 614,615, now abandoned, 614,617, now abandoned 614,491, all filed May 29, 1984. This is also a continuation-in-part of U.S. patent application Ser. No. 035,652 filed Apr. 6, 1987 which is a continuation-in-part of U.S. patent application Ser. No. 858,594 filed Apr. 30, 1986. U.S. patent application Ser. No. 614,612 issued as U.S. Pat. No. 4,760,025 on Jul. 26, 1988.

FIELD OF THE INVENTION

The present invention relates to novel enzyme mutants which are derived from a precursor enzyme by replacing or modifying at least one catalytic functional group of an amino acid residue in a precursor enzyme. Such mutant enzymes have a catalytic preference for substrates which provide the replaced or modified catalytic group or its equivalent functional group such that the substrate, in essence, together with the enzyme mutant, assists in its own catalytic conversion to product(s).

PREFILLING DISCLOSURES

Enzymes are polypeptides which catalyze a wide variety of chemical reactions. It is generally accepted that enzymatic catalysis requires that the substrate bind to the enzyme in the region of the enzyme's active site such that the specific region being acted upon by the enzyme is distorted into a configuration approximating the transition state of the reaction being catalyzed. In many cases the specific site of catalysis within the substrate must be oriented so that specific residues of the enzyme involved in catalysis can act on the bound and distorted substrate. Thus, within the active site, amino acid residues can generally be characterized as those primarily involved in substrate binding and hence determinative of substrate specificity and those involved primarily with the actual chemical catalysis, e.g., those involved in proton or electron transfer or nucleophilic or electrophilic attack on the substrate.

A wide variety of classical methods have been used to deduce the binding and catalytic residues in the active site of an enzyme. For example, the X-ray crystal structures of the serine endoprotease subtilisin containing covalently bound peptide inhibitors (Robertus, J. D., et al. (1972) *Biochemistry* 11, 2439-2449), product complexes (Robertus, J. D., et al. (1972) *Biochemistry* 11, 4293-4303), and transition state analogs (Matthews, D. A., et al. (1975) *J. Biol. Chem.* 250, 7120-7126; Poulos, T. L., et al. (1976) *J. Biol. Chem.* 251, 1097-1103), which have been reported have provided information regarding the active site of subtilisin including the amino acid residues involved in substrate binding and catalytic activity. In addition, a large number of kinetic and chemical modification studies have been reported for subtilisin which have also aided in deducing the substrate binding and catalytic residues of subtilisin (Philip, M., et al. (1983) *Mol. Cell. Biochem.* 51, 5-32; Svendsen, I. B. (1976) *Carlsberg Res. Comm.* 41, 237-291; Markland, F. S. et al. (1971) In *The Enzymes* Ed. Boyer, P. D., Academic Press, New York, Vol. 3, pp. 561-608). In most cases where the chemical modification was to a catalytic amino acid residue, the enzymatic activity of the enzymes modified was destroyed or severely impaired (Fersht, A. (1977) "Enzyme Mechanism and Structure", William Freeman, San Francisco, Calif., pp. 201-205). In two reported examples, chemical modification of the active site serine of subtilisin resulted in the replacement of the serine-OH with —SH which produced a modified enzymatic activity (Neet, K. E., et al. (1968) *J. Bio. Chem.* 248, 6392-6401; Polgar, L., et al. (1967) *Biochemistry* 6, 610-620). Most chemical modifications of catalytic residues, however, necessarily maintain or increase the effective side chain volume of the amino acid modified and consequently maintain or decrease the effective volume within which the catalytic residues must function.

The recent development of various in vitro techniques to manipulate the DNA sequences encoding naturally-occurring polypeptides as well as recent developments in the chemical synthesis of relatively short sequences of single and double stranded DNA has resulted in the reported synthesis of various enzymes wherein specific amino acid residues have been substituted with different amino acids (Ulmer, K. M. (1983) *Science* 219, 666-671).

There are several reported examples where a catalytic residue of a particular enzyme has been substituted with a different amino acid. Some of these references describe the replacement of a catalytic amino acid with an amino acid having a side chain functional group different from that of the catalytic amino acid being replaced e.g. substitution of a neutral polar side chain moiety for a side chain moiety containing an acid group or substitution of one nucleophilic side chain moiety with a different nucleophilic moiety. Others describe replacements where the side chain functional group of a catalytic residue remained constant but the position of that functional group was moved within the active site.

For example, Aspartate-102 of eucaryotic trypsinogen is reported to be a catalytic residue required for endoprotease activity. Roczniak, S. O., et al. (1985), *J. Cell Biochem* 9B (Abstracts) p. 87 briefly report the substitution of asparagine for aspartate at position 102. In this case, the carboxylate of aspartic acid was effectively substituted with the polar neutral side chain of asparagine which reportedly resulted in a dramatic decrease in $k_{cat}$.

Dalbadie-McFarland, G., et al. (1982) *Proc. Natl. Acad. Sci. (USA)* 79, 6409-6413, report the inversion of the ser-thr diad of the β-lactamase gene contained in plasmid pBR322. This inversion resulted in the conversion of the catalytically active Serine-70 to Threonine and reportedly produced a mutant with an ampicillin-sensitive phenotype.

The substitution of Serine-70 in β-lacatamase with cysteine is reported by Sigal, I. S., et al. (1984) *J. Biol. Chem.* 259, 5327-5332. This replacement of an active site serine by a cysteine residue results in the net substitution of an —OH group by an —SH group, each of which can be effective nucleophiles. The thiol-containing β-lactamase reportedly catalyses the hydrolysis of β-lactams with a substrate specificity that is distinct from that of the wild type enzyme. For benzyl penicillin and ampicillin, the $K_m$ values are similar to wild type values although the $k_{cat}$ values are 1–2% that of a wild type enzyme. However, when reacted with the cephalosporin nitrocefin, the $K_m$ is greater than 10 fold that of the wild type and the $k_{cat}$ is at least as large as the $k_{cat}$ for the wild type enzyme.

In Strauss, et al. (1985) *Proc. Natl. Acad. Sci. (USA)* 82, 2272–2276, triosphosphate isomerase was reportedly modified to replace glutamic acid at position 165 with aspartic acid. This replacement does not alter the chemical nature of the side chain at position 165 but rather moves the catalytic carboxyl group at that position, in essence, by the removal of a methylene group from glutamic acid. The $k_{cat}$ for different substrates was dramatically altered by this mutation leading the author to conclude that glutamic acid at position 165 is critical for proton shuttling during catalysis and further suggesting that this residue makes only a small contribution to the binding of the reaction intermediates.

The substitution of Serine-102 in the active site of alkaline phosphatase with cysteine is reported by Ghosh, S. S., et al. (1986) *Science* 231, 154–148. The resulting thiol enzyme catalyzes the hydrolysis of a variety of phosphate monoesters. The authors hypothesize, however, based on the observed catalytic efficiency of the thiol containing enzyme, that the serine to cysteine mutation results in a change in the rate-determining step of catalysis from dephosphorylation to the formation of a phosphoryl-enzyme intermediate.

The substitution of different amino acids for putative catalytic residues in various enzymes has been directed to the determination of whether these residues are primarily involved in catalysis rather than substrate binding. In several reported cases, however, the expected result was not obtained. In Gardell, S. J. et al. (1985) *Nature* 317, 551–555, Tyrosine-248 in carboxypeptidase A from rat was substituted with phenylalanine. Tyrosine-248 had previously been thought to play a role in catalysis through its phenolic side chain. The particular substitution described removed the phenolic hydroxide moiety of tyrosine by substitution with phenylalanine. The authors report that the catalytic reactivity of the wild type enzyme compared to the substituted enzyme containing phenylalanine at position 248, for certain substrates, indicated that Tyrosine-248 was not obligatory for the hydrolysis of peptide substrates. Rather, the authors suggest that the Tyrosine-248 hydroxyl group participates in substrate binding rather than catalysis.

Similarly, Threonine-113 in dihydrofolate reductase from *E. coli* is a strictly conserved residue at the dihydrofolate binding site which interacts with a second conserved residue, Aspartate-27, via a hydrogen bond and presumably with the substrate dihydrofolate indirectly through a water molecule (Jin-Tann Chen, et al. (1985) *J. Cell. Biochem* 29, 73–82). Since Aspartate-27 is also conserved and involved in catalysis, this suggested to the authors that Threonine-113 could be required for proton transfer during catalysis. The authors report the substitution of Threonine-113 with valine and conclude that Threonine-113 is not involved in catalysis since there is no loss of catalytic efficiency upon substitution with valine.

Schultz, S. C., et al. (1986) *Proc. Natl. Acad. Sci. (USA)* 83, 1588–1592, report the substitution of threonine-71 in class A β-lactamase with all possible amino acid substitutions to determine the role of this residue. Threonine-71 is a residue in the conserved triad Ser-Thr-Xaa-Lys. The results obtained by these authors suggests that Threonine-71 is not essential for binding or catalysis, as expected, but is important for stability of the β-lactamase protein.

Much of the work involving the substitution of different amino acids in various enzymes has been directed to the substitution of amino acid residues involved in substrate and transition-state binding. Examples include the substitution of single amino acids within the active site of tyrosyl-tRNA synthetase (Cysteine-35→Serine, Winter, G. et al. (1982) *Nature* 299, 756–758; Cysteine-35→Glycine, Wilkinson, A. J. et al. (1983) *Biochemistry* 22, 3581–3586; and Threonine-51→Alanine and Threonine-51→Proline, Wilkinson A. J. et al. (1984) *Nature* 307, 187–188).

Other examples of substitutions of amino acids involved in substrate binding include a double mutant of tyrosyl-tRNA synthetase involving Cysteine-35→Glycine together with Threonine-51→Proline (Carter, P. J. et al. (1984) *Cell* 38, 835–840); the substitution of glycine residues at positions 216 and 226 of rat pancreatic trypsin with alanine residues to produce two single substitutions and one double substitution (Craik, C. S. et al. (1985) *Science* 228, 291–297); and the substitution of various non-catalytic residues in dihydrofolate reductase (Villafranca, J. E., et al. (1983) *Science* 222, 782–788).

Paluh, J. L., et al. (1984) *J. Biol. Chemistry* 260, 1188–1894, report the substitution of Cysteine-84 with glycine in *Serratia marcescens* anthranilate synthase Component II. They report that this replacement abolished the glutamine-dependent anthranilate synthase activity but not the ammonium-dependent activity of the enzyme. They also conclude that the mutation provides further evidence for the role of the active site Cysteine-84 in the glutamine amide transfer function of the enzyme. The authors also note, however, that the specific amino acid replacement might cause a relatively minor structural alteration that could abolish a glutamine binding or amide transfer independent of the function of Cysteine-84. It is not clear from this reference whether Cysteine-84 is a residue involved in binding, or actual catalysis.

The substitution of amino acid residue believed to be involved in transition state stabilization of various enzymes have also been reported. Such work has recently been summarized in Fersht, A. R., et al. (1986), *Trends in Biochemical Sciences*, 11, 321–325.

In addition to the foregoing, proteases have been used for site-specific proteolysis. Site-specific proteolysis is a powerful and often essential tool for recovery of heterologous proteins expressed as larger fusion proteins for peptide mapping, and for analysis of structure and folding by dissection of proteins into functional domains (Jacobsen, H., et al. (1974), *Eur. J. Biochem.*, 45, 623–627) or separate folding units (Richards, F. M., et al. (1959), *J. Biol. Chem.*, 234, 1459–1465). Proteolysis is preferable to chemical cleavage for recovery of functional proteins because chemical methods have limited specificities and usually require extreme conditions that can lead to unwanted side reactions and product heterogeneity.

Although a number of proteases have been used for site-specific proteolysis (Nagai, K., et al. (1987), *Methods Enzymol.*, 153, 461–481; Craik, C. S., et al. (1985), *Science*, 228, 291–297; Germino, J., et al. (1984), *Proc.*

*Natl. Acad. Sci.*, 81, 4692–4696; Reinach, F. C., et al. (1986), *Nature*, 322, 80–83), none appears to be ideally suited. The utility of these proteases is limited by their substrate specificities (leading to undesirable or incomplete cleavage products) and instabilities in detergents, reductants, or at high temperatures, which may be necessary conditions for solubilizing fusion proteins and making the target site accessible for hydrolysis. Furthermore, many of these proteases, especially mammalian blood-clotting enzymes (Nagai, K., et al. (1987), supra) are unavailable in large quantities and in highly purified forms so that they are free of other proteolytic activities. Subtilisin BPN' most nearly satisfies all of these requirements for a site-specific protease. Although wild-type subtilisin has been used to obtain specific proteolytic fragments (Jacobsen, H., et al. (1974), Supra; Richards, F. M., et al. (1959), supra), its substrate specificity is much too broad to be generally useful.

A reference in another field is Rossman, M. G., et al. (1985) *Nature* 317, 145–153 wherein the RNA of a human rhino virus is postulated to act as a proton acceptor for the autocatalytic cleavage of the viral coat protein VPO into VP2 and VP4.

The references discussed above are provided solely for their disclosure prior to the filing date of the present case, and nothing herein is to be construed as an admission that the inventors are not entitled to antedate such disclosure by virtue of prior invention or priority based on earlier filed applications.

Based on the above references, however, it is apparent that those skilled in the art have focused on altering enzyme specificity by changing substrate and transition-state binding residues. It has heretofore not been recognized that residues containing side chains directly involved in catalysis can be substituted with residues containing smaller and catalytically inactive side chains to produce enzyme mutants which are catalytically active with substrates which provide the catalytic function of the replaced residue side chain. Thus, these enzyme mutants have a substrate specificity which is distinguished primarily at the level of catalysis rather than substrate binding.

Accordingly, it is an object herein to provide enzyme mutants wherein at least one catalytic group of an amino acid residue of a precursor enzyme is replaced or modified such that the thus formed mutant enzyme has a preferred catalytic activity for a substrate which is capable of providing the replaced or modified catalytic function when in contact with the mutant enzyme.

It is a further object to provide DNA sequences encoding such enzyme mutants as well as expression vectors containing such mutant DNA sequences.

Still further, another object of the present invention is to provide host cells transformed with such vectors as well as host cells which are capable of expressing such enzyme mutants either intracellularly or extracellularly.

A further object of the present invention is to provide a catalytically active mutant enzyme substrate complex wherein at least one of the catalytic functional group of the complex is provided by the substrate.

Still further, an object of the present invention is to provide processes wherein the enzyme mutants of the invention are contacted with modified substrates to bring about desired enzymatic catalysis.

Further, it is an object of the invention to provide fusion polypeptide containing a target sequence which is reactive with the enzyme mutants of the invention.

Still further, it is an object herein to provide solid supports containing the enzyme mutants of the invention as well as methods utilizing such solid support.

A further object is to provide methods for purifying the enzyme mutants of the invention.

SUMMARY OF THE INVENTION

The invention includes enzyme mutants not found in nature which are derived from a precursor enzyme by the replacement or modification of at least one catalytic group of an amino acid residue which when in contact with a selected region of a polypeptide substrate functions catalytically therewith. The enzyme mutant so formed is relatively inactive catalytically with the corresponding substrate as compared to the mutant's catalytic activity with a modified substrate formed by replacing or modifying a moiety in a selected region of the precursor enzyme's substrate. This selected region of the substrate is modified to include the catalytic group, or its equivalent which is replaced or modified in the precursor enzyme, such that the enzyme mutant is catalytically active with the modified substrate.

The invention also includes mutant DNA sequences encoding such mutant enzymes, expression vectors containing such mutant DNA sequences and host cells transformed with such vectors which are capable of expressing said enzyme mutants.

The invention also includes a catalytically active enzyme-substrate complex comprising an enzyme mutant and a modified substrate. The enzyme mutant is not found in nature and is derived from a precursor enzyme by the replacement or modification of at least one catalytic group of an amino acid residue which, when in contact with a selected region of a substrate for the precursor enzyme, functions catalytically with such substrate. The enzyme mutant so formed is relatively inactive with the substrate for the precursor enzyme as compared to the enzyme mutant's catalytic activity with a modified substrate. The modified substrate is formed by replacing or modifying a moiety in the selected region of the precursor enzyme's substrate. This selected region of the substrate is modified to include the catalytic group, or its equivalent, which is replaced or modified in the precursor enzyme such that the enzyme mutant is catalytically active with the modified substrate.

The invention further includes a process comprising contacting an enzyme mutant and a modified substrate to produce substrate assisted catalysis of the modified substrate. In this aspect of the invention, the enzyme mutant is the same as that defined for the enzyme mutant-substrate complex of the invention.

The invention also includes fusion polypeptides comprising an amino terminal portion, a carboxy terminal portion and a target cleavage sequence between the amino and carboxy terminal portions. The target cleavage sequences comprises amino acid residues $P_4$, $P_3$, $P_2$ and $P_1$ where $P_2$ is histidine. This target cleavage site is reactive with H64A mutant subtilisins.

The invention further includes subtilisin mutants comprising the amino acid sequence of *B. amyloliquefaciens* subtilisin or equivalents thereof wherein the mutant amino acid sequence contains the substitution H64A alone or in combination with substitutions at other residues.

Further, the invention includes processes for cleaving the above fusion polypeptides with the above H64A mutant subtilisins.

Further, the invention includes processes for purifying H64A subtilisin mutants wherein at least one surface amino acid residue of a H64A subtilisin mutant is substituted to contain cysteine. The cysteine-containing mutant is thereafter contacted with chromatographic material having an affinity for cysteine.

BRIEF DESCRIPTION OF THE DRAWINGS

FIG. 1 is the DNA and amino acid sequence for B. amylolquefaciens subtilisin.

FIG. 2 depicts catalytic residues of B. amyolquefaciens subtilisin.

FIGS. 3A and 3B depict the amino acid sequence of subtilisin as obtained from various sources.

FIG. 3C depicts the conserved residues of B. amyloquefaciens subtilisin when compared to a number of other subtilisin sequences.

FIG. 4 is a schematic diagram showing the substrate binding cleft to subtilisin together with a substrate.

FIG. 5 is a stereo view of B. amolquefaciens subtilisin containing a modeled bound peptide substrate having the sequence L-Phe-L-Ala-L-His-L-Tyr-L-Gly-L-Phe representing residues P4 to P2' of the substrate.

FIG. 6 depicts the plasmid PS4.

FIGS. 7A and 7B depict the pH dependence of hydrolysis of N-succinyl-L-Phe-L-Ala-L-Ala-L-Phe-p-nitroanilide substrate (sFAAF-pna) by S24C:H64A subtilisin BPN'.

FIG. 7C depicts the pH dependence for hydrolysis of N-succinyl-L-Phe-L-Ala-L-His-L-Phe-p-nitroanilide substrate (sFAHF-pna) by S24C:H64A subtilisin BPN'.

FIGS. 8A and 8B depict the hydrolysis of a polypeptide substrate by S24C:H64A and S24C subtilisin BPN'.

FIG. 9 depicts a stereo view of a complex between bovine trypsin and pancreatic trypsin inhibitor complex.

FIG. 10 is a stereo view of a substrate model (filled atoms) L-Phe-L-Ala-L-His-L-Tyr-L-Ala-L-Phe bound to the active site of Bacillus amyloiquefaciens subtilisin BPN' (open atoms). This model shows the superposition of the catalytic histidine (H64) with the substrate P2 histidine. The substrate may be represented as:

where the scissile peptide bond is between the P1 and P1' residues (Schechter, I., et al. (1967), Biochem. Biophys. Res. Commun., 27, 157–162).

FIG. 11 depicts the activity of S24C:H64A subtilisin BPN' with sFAHF-pna in the presence of (A) salts: KCl (O), NaCl (●); (B) denaturants: urea (□), guanidine hydrochloride (GuHCl, ■ ), (C) anionic detergents: SDS (●), sodium deoxycholate (□) and nonionic detergents: nonidet P-40 (O), tween 20 (■).

FIG. 12 depicts the construction of phagemid pZAP encoding a fusion protein for the signal (S) and one synthetic domain for Staphylococcus aureus protein A (Z) followed by a histidine-containing linker (L) and then E. coli alkaline phosphatase (AP). The residues in the target site to be cleaved by the engineered subtilisin BPN' variant are designated P4 through to P2' (scissile bond indicated by large arrow).

FIG. 13 depicts digestion of the Z-AP fusion protein with mutant subtilisins. 200 pmol Z-AP was incubated without enzyme or with 10 pmol of either S24C:H64A or S24C:H64A:E156S:G169A:Y217L subtilisin BPN' variants in 100µl 100 mM Tris-HCl at pH 8.60, 1 mM PMSF, 0.1% (v/v) tween 20 in the presence (+) or absence (−) or 2M KCl at 37° C. for the times indicated (hr). Samples were analyzed by SDS-PAGE. Molecular weight standards ($M_r$) have sizes in kilodaltons as indicated.

FIG. 14 depicts the combination of the plasmid encoding fusion protein Z-bIGF-I, showing details of the target cleavage sequence and the junction with the protein A Z domain and b-IGF-I.

FIG. 15 shows the mass spectrum obtained from bIGF-I isolated from Z-bIGF-I after cleavage with S24C:H64A:E156S:G169A:Y217L subtilisin BPN'.

FIG. 16 is a stereo view of subtilisin BPN' showing the location of the catalytic triad (Ser221, His64 and Asp32) in relation to residue 24 which was used for immobilization of the enzyme after mutating it to cysteine (S24C). The distance between CA His64 and CA Ser24 is 24Å. Additional residues (Thr22 and Ser87) are also shown.

FIG. 17 demonstrates the effect of imidazole on the non-histidine-containing substrate sFAAF-pna by S24C:H64A subtilisin BPN'.

DETAILED DESCRIPTION OF THE INVENTION

The inventors have discovered that a catalytic group in an amino acid side chain in an enzyme can be replaced or modified to produce a mutant enzyme which is reactive with substrates which contain the replaced or modified catalytic group. The replaced or modified catalytic group is located in the substrate such that it is able to assist, with the mutant enzyme, in the catalysis of the modified substrate.

Specifically, B. amyloliquefaciens subtilisin, an alkaline bacterial protease, has been mutated by modifying the DNA encoding subtilisin to encode the substitution of the catalytic residue His-64 with alanine. As expected, $k_{cat}$ and the catalytic efficiency, as measured by $k_{cat}/K_m$, of this mutant enzyme was significantly reduced as compared to the wild type subtilisin when contacted with substrates readily cleaved by wild type subtilisin. Surprisingly, various substrates containing histidine in the P2 position were preferred by the Ala-64 mutant subtilisin.

Previous studies have focused on altering enzyme specificity by changing residues on the enzyme that bind the substrate. The alternative approach described herein, termed "substrate-assisted catalysis ", is applicable to a wide range of enzymes and substrates other than those specifically disclosed herein. In general, the invention is applicable to any enzyme in which part of the enzyme is removed and appropriately supplied by a similar functionality from a bound substrate. In this way substrates are distinguished primarily at the level of catalysis instead of binding, permitting the design of extremely specific enzyme mutants.

Since, in the case of proteases, such enzyme mutants have a specificity for substrates having the catalytic functionality which the mutant enzyme lacks, it is possible to design fusion polypeptides containing a target cleavage sequence which provides a similar functionality. In so doing, the reactivity of the fusion polypeptide with the mutant proteases of the invention is significantly restricted to the target cleavage sequence.

As used herein, "enzymes " are polypeptides which either alone or in conjunction with various co-factors catalyze a covalent change in a substrate. Enzymes can be categorized according to a systematic nomenclature and classification which has been adopted on the recommendation of the International Enzyme Commission. Thus, enzymes can be categorized as oxidoreductases (enzymes involved in oxidation reduction reactions), transferases (enzymes involved in the transfer of functional groups), hydrolases (enzymes involved in hydrolytic reactions), lyases (enzymes catalyzing addition reactions to double bonds), isomerases (enzymes involved in isomerization reactions) and ligases (enzymes involved in the formation of bonds with ATP cleavage). See, generally, Lehninger, A. L., *Biochemistry*, Worth Publishers, Inc., New York, N.Y. (1970), pp. 147–187.

A "precursor enzyme" refers to an enzyme in which a catalytic amino acid residue can be replaced or modified to produce a mutant enzyme. Typically, the DNA sequence encoding the precursor enzyme may be modified to produce a mutant DNA sequence which encodes the substitution of one or more catalytic amino acids in the precursor enzyme amino acid sequence. Suitable modification methods are disclosed herein and in EPO Publication No. 0130756 published Jan. 9, 1985. The precursor enzyme, however, can also be modified by means other than recombinant DNA technology to produce the mutant enzyme of the invention.

A precursor enzyme may also be a recombinant enzyme which refers to an enzyme for which its DNA has been cloned or to an enzyme in which the cloned DNA sequence encoding an enzyme is modified to produce a recombinant DNA sequence which encodes the substitution, deletion or insertion of one or more amino acids in the sequence of a naturally occurring enzyme. Suitable methods to produce such modifications include those disclosed herein and in EPO Publication No. 0130756. For example, the subtilisin multiple mutant herein containing the substitution of serine at amino acid residue 24 with cysteine and the substitution of histidine at amino and residue 64 with alanine can be considered to be derived from the recombinant subtilisin containing the substitution of cysteine for serine at residue 24. The mutant thus is produced by the substitution of alanine for histidine at residue 64 in the Cys-24 recombinant subtilisin. The resulting double mutant is designated S24C:H64A where the single letter code (Creighton, Thomas E. (1984) Proteins, Structures and Molecular Properties, International Student Edition, W. H. Freeman and Company, p. 7) for the wild-type amino acid is followed by residue number and the amino acid replacement.

Other examples of recombinant subtilisin which have been modified to substitute alanine for histidine at residue 64 include the following: S24C:G166A, S24C:G166A, S24C:E156S:G169A:Y217L and S24C:E156S:G166A:G169A:Y217L. These particular recombinant subtilisin mutants were combined with the H64A mutation to increase the catalytic activity of such mutants with substrates providing the missing histidine functionality in the mutant subtilisin.

Carbonyl hydrolases are enzymes which hydrolyze compounds containing

bonds in which X is oxygen, nitrogen or sulfur. They include naturally-occurring carbonyl hydrolases and recombinant or chemically synthesized carbonyl hydrolases. Naturally occurring carbonyl hydrolases principally include hydrolases, e.g. lipases and peptide hydrolases, e.g. subtilisins or metalloproteases. Peptide hydrolases include α-aminoacylpeptide hydrolase, peptidylamino-acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

Subtilisins are bacterial carbonyl hydrolases which generally act to cleave peptide bonds of proteins or peptides. As used herein, "subtilisin" means a naturally occurring subtilisin or a recombinant subtilisin. A series of naturally occurring subtilisins is known to be produced and often secreted by various bacterial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however, is histidine-aspartate-serine. Thus, subtilisin herein refers to a serine protease having the catalytic triad of subtilisin related proteases.

Carbonyl hydrolases and their genes may be obtained from many procaryotic and eucaryotic organisms. Suitable examples of procaryotic organisms include gram negative organisms such as *E. coli* or pseudomonas and gram positive bacteria such as micrococcus or bacillus. Examples of eucaryotic organisms from which carbonyl hydrolase and their genes may be obtained include yeast such as *S. cerevisiae*, fungi such as Aspergillus sp., and mammalian sources such as, for example, Bovine sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, carbonyl hydrolase as used herein has a functional definition which refers to carbonyl hydrolases which are associated, directly or indirectly, with procaryotic and eucaryotic sources.

An "enzyme mutant" has an amino acid sequence which is derived from the amino acid sequence of a "precursor enzyme" and has a catalytic preference for a modified substrate or a target cleavage sequence as defined herein. The amino acid sequence of the enzyme mutant may be "derived" from the precursor amino acid sequence by the substitution of one or more catalytic amino acid residues of the precursor amino acid sequence. Suitable methods for such manipulation of the precursor DNA sequence include methods disclosed herein and in EPO Publication No. 0130756. Other methods, for example, to directly modify the amino acid side chain of the precursor enzyme may be used provided they produce the catalytic preference for a modified substrate or a target cleavage sequence. A "catalytic amino acid residue" is one which contains a catalytic group.

As used herein in connection with enzyme mutants, a "catalytic group" in an enzyme is a functional side chain of an amino acid residue which undergoes a change in charge or chemical bonding state during a reaction sequence and which becomes regenerated at the end of the reaction sequence, or which interacts directly with such a functional side chain to facilitate its change in charge or chemical bonding state. Catalytic groups typically participate in catalysis by interacting directly or indirectly as a nucleophile, electrophile, acid, base or electron transfer agent with the reactive site of a substrate. Typical catalytic amino acid residues and their respective catalytic groups (shown in parentheses) include: Ser(—OH), Thr(—OH), Cys(—OH), Tyr(—OH), Lys(—NH$_2$), Asp(—CO$_2$H), Glu(—CO$_2$H), His(imidazolyl) and Met(—SCH$_3$). See Table I. Thus, for example, catalytic groups for *B. amyloliquefaciens* subtilisin and as shown in FIG. 2 corresponding to the amino acid position numbers referred to in FIG. 1 comprise the side chains to the amino acids Asp-32, His-64 and Ser-221.

TABLE I

| | Precursor Enzyme | | | |
|---|---|---|---|---|
| Catalytic Residue | Preferred Amino Acid Residue Substitution | Alternate Amino Acid Residue Substitution | Modified Substrate | |
| | | | Catalytic Group | Equivalent Catalytic Group |
| His | Gly, Ala | Ser | Imidazoyl | —NH$_2$ |
| Lys | Gly, Ala, Ser | Thr, Leu, Asn | —NH$_2$ | Imidazolium |
| Ser | Gly | Ala | —OH | —SH |
| Thr | Gly | Ala | —OH | —SH |
| Cys | Gly | Ala | —SH | —OH |
| Asp | Gly, Ala | Ser | —CO$_2$H | Imadazoyl, Phenol |
| Glu | Gly, Ala, Ser | Thr, Cys | —CO$_2$H | Imadazoyl, Phenol |
| Tyr | Gly, Ala, Ser, Asn, Gln | Thr, Cys | Phenol | —OH, —SH Imidazolium |
| Met | Gly, Ala | Ser, Thr | —S—CH$_3$ | —SH |
| Phe | Gly, Ala, Ser | Leu, Val | Phenyl | —S—CH$_3$, Phenol |
| Trp | Gly, Ala, Ser | Leu, Val | Indole | —S—CH$_3$, Phenol, Phenyl |

As used herein in connection with the enzyme-substrate complexes or processes of the invention, a "catalytic group" in addition to the above definition, includes functional side chains of amino acid residues which aid in stabilizing the transition state of a reaction by interacting directly or indirectly with a polarized or charged transition state. Such transition state stabilization is typically achieved by the formation of salt bridges or the creation of a dipole-dipole interaction (e.g. hydrogen bond formation) between the transition state and the catalytic residues stabilizing it. Typical catalytic amino acid residues involved in transition state stabilization and their respective catalytic groups (shown in parenthesis) include those catalytic residues of Table I:

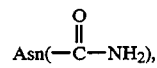

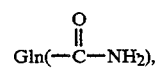

and

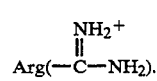

(See Table II). For the *B. amyloliguefaciens* subtilisin shown in FIGS. 1 and 2, a catalytic residue involved in transition state stabilization is Asn-155 which provides a hydrogen bond to stabilize the oxyanion of the tetrahydral intermediate shown in FIG. 2.

Many enzymes are sufficiently characterized such that the catalytic groups of these enzymes (as defined above) are well known to those skilled in the art. However, for those enzymes which are not so characterized, the catalytic residues can be readily determined.

In this regard, amino acid replacement or chemical modification of catalytic groups (including those directly involved in catalysis and those involved in transition state stabilization) typically cause large disruptions in the catalytic step of the reaction (e.g. often measured by kcat) and little effect on the enzyme substrate dissociation constant (e.g. often measured by K$_m$).

Thus, to determine whether a putative catalytic group is indeed catalytic, one skilled in the art can replace or modify the residue containing that group as described herein. If such substitution or modification abolishes or significantly reduces k$_{cat}$, but does not substantially effect K$_m$ (e.g. increases or decreases K$_m$ by a factor of 50 or preferably 10 or less), the side chain of the residue substituted is a catalytic group.

Structural methods such as x-ray crystallography and nuclear magnetic resonance spectroscopy (nmr) can also be used to identify potential catalytic groups by their proximity to the site of the substrate chemical bond which becomes altered. Chemical, kinetic and

TABLE II

| | Precursor Enzyme | | | |
|---|---|---|---|---|
| Catalytic Residue | Preferred Amino Acid Residue Substitution | Alternate Amino Acid Residue Substitution | Modified Substrate | |
| | | | Catalytic Group | Equivalent Catalytic Group |
| Asn | Gly, Ala, | Thr, Ser, Cys | O=C—NH$_2$ | —OH Imidazoyl |
| Gln | Gly, Ala, | Thr, Ser, Cys | O=C—NH$_2$ | —OH Imidazoyl |
| Arg | Gly, Ala, | Thr, Ser, Cys | +NH$_2$=C—NH$_2$ | —NH$_3^+$ Imidazolium | nmr methods can also be useful in identifying catalytic groups by showing a change in their charge or chemical bonding properties during a reaction.

Alternatively, if a particular enzyme is not well characterized but is closely related to an enzyme wherein one or more catalytic groups are already well-defined, the catalytic groups in that enzyme may be identified by determining its equivalent catalytic residues.

Thus, for example, a catalytic residue (amino acid) of a precursor carbonyl hydrolase is equivalent to a residue of *B. amyloliquefaciens* subtilisin if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

In order to establish homology to primary structure in the above example, the amino acid sequence of a precursor carbonyl hydrolase is directly compared to the *B. amyloliquefaciens* subtilisin primary sequence and particularly to a set of residues known to be invariant in all subtilisins for which sequence is known (FIG. 3C). After aligning the conserved residues, allowing for necessary insertions and deletions in order to maintain alignment (i.e., avoiding the elimination of conserved residues through arbitrary deletion and insertion), the residues equivalent to the catalytic amino acids (His-64, Asp-32, Ser-221, Asn-155) in the primary sequence of *B. amyloliquefaciens* subtilisin are defined. Alignment of conserved residues preferably should conserve 100% of such residues. However, alignment of greater than 75% or as little as 20% of conserved residues is also adequate to define equivalent residues.

For example, in FIG. 3A the amino acid sequence of subtilisin from *B. amyloliquefaciens* (BPN') *B. subtilisin* var. I168 and *B. lichenformis* (Carlsbergensis) are aligned to provide the maximum amount of homology between amino acid sequences. A comparison of these sequences shows that there are a number of conserved residues contained in each sequence. These residues are identified in FIG. 3C.

These conserved residues thus may be used to define the corresponding equivalent catalytic amino acid residues of *B. amyloliquefaciens* subtilisin in other carbonyl hydrolases such as thermitase derived from Thermoactinomyces. These two particular sequences are aligned in FIG. 3B to produce the maximum homology of conserved residues. As can be seen there are a number of insertions and deletions in the thermitase sequence as compared to *B. amyloliquefaciens* subtilisin. Thus, the equivalent catalytic amino acid of Asn-155 in *B. amyloliquefaciens* subtilisin in thermitase is the particular lysine shown beneath Asn-155.

Equivalent catalytic residues homologous at the level of tertiary structure for a precursor carbonyl hydrolase whose tertiary structure has been determined by x-ray crystallography, are defined as those for which the atomic coordinates of 2 or more of the main chain atoms of a particular amino acid residue of the precursor carbonyl hydrolase and *B. amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of nonhydrogen protein atoms of the carbonyl hydrolase in question to the *B. amyloliquefaciens* subtilisin. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent catalytic residues which are functionally analogous to a catalytic residue of *B. amyloliquefaciens* subtilisin are defined as those amino acids of the precursor carbonyl hydrolases which may adopt a conformation such that they either alter, modify or contribute to catalysis in a manner defined and attributed to a specific catalytic residue of the *B. amyloliquefaciens* subtilisin as described herein. Further, they are those residues of the precursor carbonyl hydrolase ( for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of a catalytic group of *B. amyloliquefaciens* subtilisin. The three dimensional structures would be aligned as outlined above.

As indicated, amino acid residues of *B. amyloliquefaciens* subtilisin have been modified by substitution with a different amino acid to increase the catalytic activity of H64A mutants, e.g., at residues G166, E156, G169, Y217. Equivalent residues in other carbonyl hydrolases may be similarly identified as homologous to the primary sequence or to the tertiary structure of *B. amyloliquefaciens* subtilisin. Further, equivalent residues may be identified as functionally analogous to a particular residue of *B. amyloliquefaciens* subtilisin. In this regard specific reference is made to EPO Publication No. 0251446.

As used herein, a "substrate" refers to a substrate which is reactive with a precursor enzyme. For those enzymes which utilize polypeptides as substrate, the substrate is typically defined by an amino acid sequence which is recognized by the precursor enzyme to bind the substrate therewith. For example, a substrate for trypsin contains the amino acid sequence $$X_1—K—X_2$$

or $$X_1—R—X_2$$

where $X_1$ is any $P_2$ amino acid, $X_2$ is a $P_1'$ amino acid except Pro, R is Arg and K is Lys. Subtilisin is broadly specific and will cleave a wide range of polypeptide substrates albeit at substantially different rates. An example of a substrate which is efficiently cleaved is the sequence FAAY ↓ AF (at the point designated by the arrow) where F, A, Y are Phe, Ala and Tyr, respectively, and Tyr occupies the $P_1$ position (see FIG. 4). These residues, in general, are those recognized by the enzyme to bind a particular substrate and are referred to herein as a "selected region" of the substrate. Of course, there may be a wide range of polypeptides which are substrates for a particular precursor enzyme. However, each of these substrates will contain a selected region recognized by the precursor enzyme.

In various aspects of the invention, the substrate may be a non-proteinatious molecule such as a nucleic acid, carbohydrate, a metabolite in a biological pathway or an antibiotic. In the case of nucleic acids and carbohydrates the "substrate" can be similarly defined as for a polypeptide substrate except that these regions are defined not by amino acid sequence but rather by nucleic acid sequence and carbohydrate sequence, respectively. Thus, for example, restriction endonucleases recognize specific DNA sequences and α amylase recognizes the α(1,4) glycosidic linkage between glucose molecules in amylose.

In the case of antibiotics, which usually are neither polypeptides, nucleic acids or carbohydrates, there is usually little problem in identifying the substrate. Thus, for example, the substrates for β lactamases are penicillins and cephalosporans.

In general, substrates for a wide range of enzymes, including the selected region of such substrates, are known to or may be readily determined by those skilled in the art.

A "modified substrate" is a substrate wherein at least one moiety contained therein is replaced or modified to form a modified moiety which includes the catalytic group replaced or modified in a precursor enzyme or the equivalent of the catalytic group so replaced or modified. The catalytic group contained in the modified substrate is positioned such that upon binding with the mutant enzyme formed by modifying a particular precursor enzyme, the modified substrate provides a modified moiety which when in contact with the mutant enzyme provides the catalytic group replaced in the precursor enzyme or its equivalent. The thus formed enzyme mutant-modified substrate complex is thereby rendered catalytically active.

In the case of precursor enzymes having corresponding polypeptide substrates, the modified substrate is also a polypeptide which contains an amino acid sequence which binds to the mutant enzyme and which contains an amino acid residue within that selected region which has a side chain catalytic group which is the same or equivalent to the amino acid replaced or modified to form the mutant enzyme. This amino acid sequence while binds to and is reactive with the mutant enzyme is sometimes also referred to as the "target cleavage sequence".

In a preferred embodiment of the invention, a family of H64A subtilisin BPN' mutants (from *B. amylolquefaciens*) are disclosed. Such H64A mutants have a specificity for target cleavage sequences designated $P_4$, $P_3$, $P_2$ and $P_1$. This designation corresponds to the analogous designation for amino acid residues in the substrate for wild type subtilisin (see FIG. 4). For the H64A mutant subtilisin, $P_2$ in the target cleavage sequence is histidine. Further, this target cleavage sequence preferably contains $P_1$ amino acids comprising tyrosine, phenylalanine, methionine, leucine, and lysine. Most preferably, $P_1$ is tyrosine or phenylalanine. The $P_4$ residue in this target cleavage sequence is preferably phenylalanine, isoleucine, methionine, alanine, leucine, lysine or valine. Most preferably $P_4$ is phenylalanine. The $P_3$ residue in the target cleavage sequence may be any amino acid but is preferably alanine, asparagine, glutamate, aspartate, isoleucine, glutamine, tyrosine, histidine, glycine, leucine, serine or valine. Most preferably $P_3$ is alanine, valine, glutamine or histidine. In many instances, the residues $P_1$ and $P_2$ are sufficient to define the target cleavage sequence such that a mutant H64A subtilisin will cleave at the C terminal side of the $P_1$ residue. However, the preferred target cleavage sequence comprises $P_4$ through $P_1$ and most preferably comprise the sequences phenylalanine-alanine-histidine-tyrosine and phenylalanine-alanine-histidine-phenylalanine.

An "equivalent" catalytic group in a modified substrate is one which is capable of reacting, combining or interacting in the same or similar manner as that which was removed from or modified in the precursor enzyme. Equivalent catalytic group refers to a group having the ability to provide a similar or equivalent catalytic role. It is not necessary that an equivalent catalytic group provide equivalent chemical structure. For example, if a catalytic His residue is removed from the enzyme, an equivalent catalytic group from the substrate would be an imidazolyl group which may be donated (but not always or exclusively) by a His side chain. If a catalytic Ser residue is removed from the enzyme an equivalent catalytic group from the substrate may be a hydroxyl group which may be donated by threonine or tyrosine side chain. In some cases the equivalent catalytic group may not be identical to the original enzyme group. Thus, an equivalent catalytic group for the Serine-OH may be the Cysteine-SH. See Tables I and II.

Upon binding with the enzyme mutant, the same or equivalent catalytic group in the modified substrate is capable of being positioned such that it is close to the original position of the side chain of the amino acid residue substituted or modified in the precursor enzyme. In this manner the catalytic function of the enzyme mutant can be greatly enhanced when the enzyme mutant binds a modified substrate.

The positioning of the catalytic group or equivalent catalytic group within the selected region of a substrate to form a modified substrate may be achieved by substituting each of the amino acid residues within the selected region with a different amino acid to incorporate the catalytic or equivalent group in the modified substrate at various positions. Such modified substrates can be readily made by the methods disclosed herein and by methods known to those skilled in the art. Thereafter, these modified substrates are contacted with the particular mutant enzyme to determine which, if any, of the modified substrates are reactive with the enzyme mutant.

Alternatively, if the crystal structure of a particular enzyme or enzyme substrate complex is known, model building may be utilized to determine how a modified substrate should be constructed. Such model building may use, for example, a FRODO program (Jones, T. A. (1978) *J. Appl. Crystallogr.* 11, 268) in conjunction with an Evans and Sutherland PS300 graphics system. For example, one can use such a program and graphic system to construct the stereo view of *B. amylolquefaciens* subtilisin shown in FIG. 5 containing a model bound peptide substrate having the sequence L-Phe-L-Ala-L-His-L-Tyr-L-Gly-L-Phe representing residues P4–P2' of the substrate.

A two-dimensional representation of the relationship between the subsites involved in subtilisin (S4 through S3') and the substrate residues involved in a substrate binding (P4 through P3') is shown in FIG. 4. Normally, the P2 position in the substrates that are typically reactive with subtilisin do not require histidine.

The model in FIG. 5 is based upon a 2.0 Å X-ray crystallographic study of product complexes bound to subtilisin. See e.g. Robertus, J. D. et al. (1972) *Biochemistry* 11, 4293; Poulos, T. L. et al. (1976) *J. Biol. Chem.* 251, 1097. The catalytic triad (Asp-32, His-64, and Ser-221) is shown with the His P2 side chain from the substrate superimposed upon the catalytic His-64. The trypsin, respectively) has the His P2 side chain optimized for H-bond distances between the imidazoyl nitrogen, N$\epsilon$2 and N$\delta$61, to the catalytic Ser and Asp, respectively. Model 2 (graphic view not shown) has idealized angles for the His P2 side chain.

TABLE III

| | Angles | | | Distance (Å) | | | |
|---|---|---|---|---|---|---|---|
| | Dihedral | | H-bond | N$\epsilon$2(his)→ | N$\delta$1(His)→ | Catalytic | His→His P2 |
| | $x^1$ | $x^2$ | (Ser→His) | Og(Ser) | O$\delta$1(Asp) or O$\delta$2(Asp) | N$\epsilon$2/N$\epsilon$2 | N$\delta$1/N$\delta$1 |
| Subtilisin Catalytic His64 (actual) His P2 side chain | −167° | 85° | 148° | 3.17 | 3.34 | 2.27 | — | — |
| Model S1 | −164° | −50° | 149° | 3.17 | 3.55 | 2.72 | 1.39 | 1.35 |
| Model S2 | −180° | −90° | 144° | 3.25 | 3.59 | 3.34 | 0.37 | 1.57 |
| Trypsin Catalytic His57 (actual) His P2 side chain | 71° | 85° | 170° | 2.70 | 3.25 | 2.70 | — | — |
| Model T1 | −155° | −79° | 179° | 2.78 | 4.78 | 3.28 | 0.98 | 2.10 |
| Model T2 | −180° | −90° | 158° | 2.48 | 5.09 | 3.76 | 0.58 | 2.09 | distances between the O$\gamma$ of Ser-221 and the corresponding N$\epsilon$Z nitrogens from His-64 and the modeled P2 His side chain are 3.17 Å and 3.17 Å, respectively. The distances between the O$\delta$Z of Asp-32 and the corresponding N$\delta$1 nitrogens from His-64 and the modeled P2 His side chain are 2.72 Å and 2.72 Å, respectively. The modeled distances between the N$\epsilon$Z and N$\delta$1 nitrogens of the histidines are 1.39 Å and 1.35 Å, respectively. The hydrogen bond distances and dihedral angles for the stereo view of the complex of FIG. 4 are given in Table III as subtilisin model S1.

Likewise, one can generate a stereo view of a complex between bovine trypsin and pancreatic trypsin inhibitor (PTI) complex in which the equivalent P2 substrate side chain (Cys-14 in PTI) is replaced by His and superimposed upon His-57 in trypsin. The coordinates for the trypsin/trypsin inhibitor complex were taken from the Brookhaven Protein Data Bank entry 2PTC deposited by R. Huber and J. Deisenhofer, 9/82. See also Deisenhofer, J., et al. (1975) *Acta. Crystallogr.*, Sect. B., 31, 238. The catalytic triad of trypsin (Ser-195, His-57, Asp-102) is shown and the carbonyl carbon of Lys-15 at the P$_1$ position in PTI is labeled. The hydrogen bond distances and dihedral angles for this stereo view in FIG. 9 are given as trypsin model T1 in Table III.

TABLE III

Pertinent bond angles and distances modeled for substrate-assisted catalysis by a His P$_2$ side chain in subtilisin or trypsin as depicted in FIGS. 5 and 9, respectively. Dihedral angles for the His side chains are defined by $x^1$(N-C$\alpha$-C$\beta$-C$\gamma$) and $x^2$(C$\alpha$-C$\beta$-C$\gamma$-C$\delta$). The hydrogen bond angles (N$\epsilon$2(His)-H$\delta$(ser)-O$\gamma$(Ser)) were calculated from the measured C$\beta$(Ser)-O$\gamma$(Ser)-N$\epsilon$2(His) angle, the N$\epsilon$2(His)-O$\gamma$(Ser) bond distance and the known O$\gamma$(Ser)-H$\delta$(Ser) distance (0.96 Å) and the C$\beta$(Ser)-O$\gamma$(Ser)-H$\delta$(Ser) bond angle (108.5°) (Weiner, S. J. et al. (1984) *J. Am. Chem. Soc.* 106, 765). H-bond distances were measured between the catalytic Ser(O) and Asp (O$\delta$1 and O$\delta$2) to the N$\epsilon$2 and N$\delta$1, respectively, from the enzyme His or the substrate His P2. The distances are given between the enzyme His and the modeled substrate His P2 N$\epsilon$2 and N$\delta$1 nitrogens. Model 1 (shown in FIGS. 5 and 9 for subtilisin and In general, modified substrates may be naturally occurring substrates containing amino acid sequences which previously were not recognized by the precursor enzyme or other enzymes or may be recombinant substrates. Thus, for example, in the former case the inventors have determined that the subtilisin mutant S24C:H64A is reactive with peptides corresponding to the naturally occurring substrates inhibin (between residues 61 and 80) and ACTH (between residues 1 and 10). See Example 9 and Table VII.

In the latter case, the recombinant substrate is engineered to be reactive with a specific enzyme mutant. Such recombinant substrates include, for example, a recombinant polypeptide containing a pro sequence (such as the Trp LE sequence from *E. coli*) and a desired polypeptide. Such recombinant polypeptides are typically generated to facilitate the expression and/or secretion of the recombinant polypeptide. However, in many instances, the sequence combined with the desired polypeptide is not cleaved selectively from the recombinant polypeptide upon secretion or by other known methods (e.g. by relatively nonspecific chemical reactions, such as treatment with CNBr, hydroxylamine, etc.).

This problem is overcome by the use of the enzyme mutants of the present invention with a "fusion polypeptide" which incorporates a target cleavage sequence which is recognized by the mutant enzyme and which will assist in its own catalytic conversion to products. Thus, as used herein, a fusion polypeptide is a recombinant polypeptide which contains an amino-terminal portion, a carboxyl-terminal portion and a target cleavage sequence interposed between the amino and carboxyl terminal portions of the recombinant polypeptide. The target cleavage sequence is reactive with a particular mutant enzyme of the invention. Fusion polypeptides may also be naturally occurring proteins that are mutated to contain the target cleavage sequence. For example, protein A and protein G bind to IgG. Protein A, or its IgG binding domain, may therefore comprise the amino terminal portion of a fusion polypeptide such that purification of the fusion polypeptide can be facilitated by affinity chromatography. Thereafter, the amino terminal portion of the fusion polypeptide together with all or part of the target cleavage sequence is removed from the desired carboxy terminal portion by cleavage with a mutant enzyme specific for the target cleavage site. Other examples of amino and carboxyl terminal portions are listed in Table IV.

TABLE IV

| Fusion Polypeptides | | |
|---|---|---|
| Amino-Terminal Portion | Target Cleavage Sequence | Carboxy-Terminal Portion |
| Protein A | e.g, optimal P₄ residues P₃, P₂, P₁ for H64A subtilisins | Surfactin(s) |
| Trp LE | | Insulin A chain |
| β galactosidase | | Insulin B chain |
| Protein G | | Pro insulin |
| Ubiquitin | | Relaxin A chain |
| Maltose binding protein | | Relaxin B chain |
| | | Pro relaxin |
| | | IGF-I |
| | | IGF-II |
| | | Brain IGF-I |
| | | DNase I |
| | | TGFα |
| | | TGFβ |
| | | Trigramin |
| | | tPA |
| | | γIfn, αIfn or βIfn |
| | | IL1 |
| | | IL2 |
| | | IL3 |
| | | TNFα |
| | | EGF |
| | | NGF |
| | | Kistrin |
| | | CD4 |
| | | Human growth hormone |

Fusion polypeptides preferably are constructed such that the target cleavage sequence is accessible to the mutant enzyme without the need to denature the fusion polypeptide after it is expressed. Thus, the amino terminal portion of the fusion polypeptide is chosen such that its C-terminal amino acid is located on or near the surface. Similarly, the carboxy terminal portion of the fusion polypeptide is preferably chosen such that its amino terminal amino acid is on or near the surface of the polypeptide forming the carboxy terminal portion. Thus, when the target cleavage sequence is interposed between the amino terminal portion and carboxy terminal portion of the fusion polypeptide, the target cleavage sequence is accessible to the mutant enzyme for catalysis.

In some instances, the particular construction of a fusion polypeptide may not result in a fusion polypeptide containing an accessible target cleavage sequence. In such cases, it is possible to denature the fusion polypeptide, either partially or completely, to facilitate catalysis. Thereafter, the desired portion of the fusion polypeptide may be renatured. Such denaturation-renaturation methods are well known to those skilled in the art.

In the case of enzyme mutants which do not act on polypeptide substrates, the modified substrate will consist of a substrate for a precursor enzyme which has been appropriately modified to contain a modified moiety which is catalytic when in contact with the enzyme mutant. Such modified substrates can be designed by substrate modeling as described above using the three-dimensional X-ray crystal structure of a precursor enzyme or enzyme-substrate complex. The construction of such modified substrates, of course, will depend upon the chemical nature of the modified substrate as determined by such modeling and could involve biochemical and/or chemical modification or synthesis of the modified substrate.

In an alternate embodiment of the invention, the catalytic group removed from the precursor enzyme is not provided by a modified substrate. Rather, the catalytic group is provided by a catalytic cofactor which contains the catalytic group removed to form the enzyme mutant or an equivalent to that catalytic group (see Tables I and II). In such an embodiment, the enzyme mutant in conjunction with the catalytic cofactor maintains the same or similar specificity for substrate as the precursor enzyme.

In a specific embodiment, the subtilisin BPN' mutant S24C:H64A formed a catalytically active mutant enzyme-substrate-cofactor complex with specific synthetic substrates and the catalytic cofactor imidazole. In the absence of imidazole, the S24C:H64A mutant had very low catalytic activity with the synthetic substrates sAAPF-pna and sFAAF-pna. Cleavage of the substrates, however, was enhanced on the addition of imidazole. Thus, the catalytic function of the imidazoyl catalytic group of histidine which in this case has been replaced with alanine can be provided by way of an appropriate catalytic group in a modified substrate or by way of an appropriate catalytic cofactor to render the mutant enzyme catalytically active.

In the case of H64A subtilisin mutants used in conjunction with a catalytic cofactor such as imidazole, preferred substrates contain an amino acid sequence corresponding to amino acid residues $P_4$, $P_3$, $P_2$ and $P_1$ of substrates efficiently cleaved by subtilisin BPN'. Particularly preferred $P_1$ residues include tyrosine, phenylalanine, methionine, leucine and lysine, most preferably phenylalanine and tyrosine. $P_2$ residues may comprise any amino acid but are most preferably alanine, glycine, proline or serine. $P_4$ residues are preferably phenylalanine, isoleucine, methionine, alanine, leucine, lysine and valine, most preferably phenylalanine. Particular $P_4$ through $P_1$ amino acids sequences useful with H64A subtilisin mutants in conjunction with imidazole include alanine-alanine-proline-phenylalanine and phenylalanine-alanine-alanine-phenylalaline.

The use of catalytic cofactors in conjunction with the mutant enzymes of the invention provides an exquisite means for controlling the catalytic activity of the enzyme mutant with substrates. Thus, the enzyme mutant of the invention and a substrate (not comprising a modified substrate) can be combined without substantial catalysis occurring until the catalytic cofactor is added.

In determining how a catalytic group should be replaced or modified in a precursor enzyme, consideration must be given to the modified substrate or catalytic cofactor and substrate with which the enzyme is targeted to be reacted with. In general, since the modified substrate will be providing a catalytic group removed from the precursor enzyme, the amino acid residue in the precursor enzyme should be replaced or modified in such a way as to provide space for the modified moiety of the modified substrate. Typically, this requires that the side chain of the precursor amino acid be reduced in volume so that the enzyme mutant can receive the moiety of the modified substrate.

The mean amino acid volume of amino acids when contained within a protein and the mean side chain volume of such amino acids normalized to a zero side chain volume for glycine are shown in Table V. As shown in Tables I and II, there are various preferred and alternate amino acids which may be substituted for specific catalytic residues within the active site of a precursor enzyme. In each case, the amino acid being substituted for a catalytic residue has a mean side chain volume which is smaller than the side chain of the catalytic residue replace. In general, the catalytic amino acid residue should be replaced with an amino acid such that the mean side chain volume change upon making the substitution is sufficient to accommodate the catalytic group or equivalent catalytic group of the modified substrate as determined empirically or by modeling studies. Thus, for example, the substitution of His-64 for Ala increases the active site volume by approximately 75 Å$^3$ (101 Å–26 Å$^3$). This increase in volume, however, is sufficient to accommodate the histidine at residue P2 in a modified substrate which has a mean side chain volume of 101 Å$^3$. Of course the detailed structure of the complex should be preferably checked by molecular modeling and ideally by X-ray crystallography to ensure that the specific side chains can interact favorably and that they are not sterically excluded even when compatible by the simple volume considerations described above.

TABLE V

| Amino Acid | Chothia(1) Mean Amino Acid Volume in Protein (Å$^3$) | Mean Side Chain Volume(2) (Å$^3$) |
|---|---|---|
| Gly | 66 | 0 |
| Ala | 92 | 26 |
| Ser | 99 | 33 |
| Cys | 118 | 52 |
| Pro | 129 | 63 |
| Thr | 122 | 56 |
| Asp | 125 | 59 |
| Val | 142 | 76 |
| Asn | 135 | 69 |
| Ile | 169 | 103 |
| Glu | 155 | 89 |
| Leu | 168 | 102 |
| Gln | 161 | 95 |
| His | 167 | 101 |
| Met | 171 | 105 |
| Phe | 203 | 137 |
| Lys | 171 | 105 |
| Tyr | 207 | 141 |
| Arg | 202 | 136 |
| Trp | 238 | 172 |

(1)Chothia (1984) Ann. Rev. Biochem. 53, 537
(2)Normalized to zero side chain volume for glycine.

In addition to providing sufficient space for the catalytic group or equivalent catalytic group of the modified substrate, the side chain functionality of the catalytic residue replaced in the precursor enzyme should be altered to facilitate the binding and catalytic activity of the modified substrate.

For example, where the side chain of a catalytic amino acid residue in the precursor enzyme contains positively or negatively charged polar groups these amino acids should be replaced or modified to contain side chain which contain non-polar or uncharged polar groups. Such substitutions are summarized in Tables I and II.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0130756 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publication No. 0130756 and further described by Yang, M. Y., et al. (1984) *J. Bacteriol.* 160, 15–21. Such host cells are distinguishable from those disclosed in PCT Publication No. 03949 wherein enzymatically inactive mutants of intracellular proteases in *E. coli* are disclosed. Other host cells for expressing subtilisin include *Bacillus subtilis* I168 (EPO Publication No. 0130756).

Host cells are transformed or transfected with vectors constructed using recombinant DNA techniques. Such transformed host cells are capable of either replicating vectors encoding the enzyme mutants or expressing the desired enzyme mutant. In the case of vectors which encode a pre or prepro form of the enzyme mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor enzyme may be obtained in accord with the general methods described in EPO Publication No. 0130756 or by other method known to those skilled in the art. As can be seen from the examples disclosed in EPO Publication No. 0130756, the methods generally comprise synthesizing labelled probes having putative sequences encoding regions of the enzyme of interest, preparing genomic libraries from organisms expressing the enzyme, and screening the libraries for the gene of interest by hybridization to the probes. Positively hybridizing clones are then mapped and sequenced.

The cloned enzyme is then used to transform a host cell in order to express the enzyme. The enzyme gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the hydrolase gene into host genome. This is facilitated by procaryotic and eucaryotic organisms which are particularly susceptible to homologous recombination.

Once the precursor enzyme gene has been cloned, a number of modifications are undertaken to enhance the use of the gene beyond synthesis of the naturally-occurring precursor enzyme. Such modifications include the production of recombinant precursor enzymes (as disclosed in EPO Publication No. 0130756) and the production of enzyme mutants.

The following cassette mutagenesis method may be used to facilitate the construction and identification of the enzyme mutants of the present invention although other methods including site-directed mutagenesis may be used. First, the gene encoding the enzyme is obtained and sequenced in whole or in part. Then the sequence is scanned for a point at which it is desired to make a mutation of one or more amino acids in the expressed enzyme. The sequences flanking this point are evaluated for the presence of restriction sites for replacing a short segment of the gene with an oligonucleotide pool which when expressed will encode various mutants. Such restriction sites are preferably unique sites within the gene so as to facilitate the replacement of the gene segment. However, any convenient restriction site which is not overly redundant in the gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Mutation of the gene in order to change its sequence to conform to the desired sequence is accomplished by M13 primer extension in accord with generally known methods. Once the gene is cloned, the restriction sites flanking the sequence to be mutated are digested with the cognate restriction enzymes and a plurality of end termini-complementary oligonucleotide cassettes are ligated into the gene. The mutagenesis is enormously simplified by this method because all of the oligonucleotides can be synthesized so as to have the same restriction sites, and no synthetic linkers are necessary to create the restriction sites.

In the disclosed embodiment, subtilisin was chosen as a model to test the concept of substrate-assisted catalysis. In the hydrolysis of peptide bonds by subtilisin, His-64 acts as a catalytic base in the formation of an acyl-enzyme intermediate and as a catalytic acid in the subsequent deacyclation step. Stroud, R. M., et al. (1975), *Proteases and Biological Control* (Cold Spring Harbor Laboratory, New York), p. 13; Kraut, J. (1977) *Ann. Rev. Biochem.* 46, 331.

The catalytic triad of subtilisin is shown in FIG. 2. As can be seen, Ser-221, His-64 and Asp-32 are positioned to facilitate nucleophilic attack by the serine hydoxylate on the carbonyl of the scissile peptide bond. Several hydrogen bonds may also help to stabilize the transition state complex for the tetrahedral substrate intermediate. One hydrogen bond is between aspartate and the positively charged histidine, N$\delta$1. Kossiakoff, A. A., et al. (1981) *Biochem.* 20, 6462–6474. A second hydrogen bond forms between the scissile amide nitrogen of the substrate and the (N$\epsilon$Z) proton on the histidine. A third set of hydrogen bonds forms between the enzyme and the oxyanion that is produced from the carbonyl oxygen of the substrate. This latter set of hydrogen bonds is formed differently by the mammalian serine proteases and subtilisin. A fourth hydrogen bond appears to exist between the amide nitrogen of the peptide bond between P-1 and P-2 and the carbonyl oxygen of Ser-125. Specifically, X-ray crystallographic studies of chymotrypsin (Henderson, R. (1970) *J. Mol. Biol.* 54, 341) indicate that two hydrogen bonds form between the substrate oxyanion and two main-chain amide protons from the enzyme (Gly-193 and the catalytic Ser-195). Crystallographic studies of subtilisin (Robertus, et al. (1972) *Biochem.* 11, 4293–4303; Matthews, et al. (1975) *J. Biol. Chem.* 250, 7120–7126; Poulos, et al. (1976) *J. Biol. Chem.* 250, 1097–1103) show that two hydrogen bonds are also formed with the oxyanion; one hydrogen bond donor is from the catalytic Ser-221 main-chain amide while the other is from one of the N$\epsilon$Z protons of the Asn-155 side chain. See FIG. 2.

The model shown in FIG. 5 revealed that the delta and epsilon nitrogens of the histidine in position P2 in the modified substrate can be superimposed within about an angstrom by the corresponding nitrogens of the catalytic His-64 (not shown in FIG. 4). This suggested that if the histidine in the catalytic triad of subtilisin was replaced by an alanine using site directed mutagenesis, a histidine from the substrate may substitute for the missing catalytic group in the mutant enzyme.

Maturation of the primary subtilisin gene product (preprosubtilisin) to subtilisin in *B. subtilis* is believed to be mediated by autoproteolysis that involves trace amounts of active subtilisin (Power, S. D., et al. (1986) *Proc. Natl. Acad. Sci USA* 83, 3096). The H64A mutation caused a severe reduction in secretion of mature subtilisin. However, it was possible to process and subsequently purify the inactive H64A mutant by co-culturing *B. subtilis* cells harboring the H64A mutant gene with *B. subtilis* cells carrying an active subtilisin gene ("helper") or by adding wild-type subtilisin. A simpler strategy of culturing *B. subtilis* cells harboring the H64A mutant in the presence of purified wild-type subtilisin BPN' (or an active mutant thereof) is also possible (Example 4).

Stringent precautions were taken to ensure the purification of H64A subtilisin away from "helper" subtilisin and any other contaminating proteases. Firstly, the mutant subtilisin was expressed in the *B. subtilis* host BG2036 described in EPO Publication No. 0130756, that was deficient in chromosomal copies of the genes for alkaline protease (subtilisin) and neutral protease. Secondly, to minimize "helper" contamination the ratio of "helper " cells to H64A cells in the fermentation culture was adjusted to 1:1,000. Thirdly, a functionally silent Ser-24→Cys mutation that is located on the surface of subtilisin (Wells, J. A., et al. (1986) *J. Biol. Chem.* 261, 6564) was introduced into the H64A mutant. This accessible cysteine served as an affinity handle for purification of the H64A mutant away from the noncysteine containing "helper" on an activated thiol sepharose column. Finally, the active "helper" subtilisin contained a functionally silent Ala-48→Glu mutation that altered its electrophoretic mobility relative to S24C:H64A on native and SDS polyacrylamide gels. After purification, the S24C:H64A mutant was judged to be greater than 99% pure by silver stained SDS (Morrissey, J. H. (1981) *Anal. Biochem.* 11, 307; Laemmli, U. K. (1970) *Nature* 227, 680) and native polyacrylamide gel electrophoresis (Example 6). These purification procedures, including the use of a helper subtilisin which is capable of electrophoretic separation from the subtilisin mutant, are not necessarily required to practice the present invention.

As indicated, in addition to the S24C:H64A mutant subtilisin, other mutations were introduced into this subtilisin mutant to increase catalytic activity. Mutations which increase the activity of wild-type subtilisin BPN' were found to have an approximately additive effect when combined (Wells, J. A., et al. (1987), *Proc. Natl. Acad. Sci.*, 84, 5167–5171). Transferring these mutations to the S24C:H64A enzyme gave incremental improvements in activity, and so provided a useful strategy for enhancing catalytic efficiency. Furthermore the preference for Tyr over Phe at the P1 position for wild-type subtilisin BPN' was also found to hold for the S24C:H64A enzyme, suggesting that this is a useful approach for substrate optimization.

Although the results on wild-type subtilisin BPN' are qualitatively similar to those with the S24C:H64A enzyme, there are significant quantitative differences. For example, the G166A mutation gave a 4-fold improvement toward the Phe substrate in the S24C:H64A enzyme yet only about a 2-fold improvement in the wild-type enzyme. Conversely, the 3 mutations (E156S:G169A:Y217L) had a larger effect upon wild-type than upon the S24C:H64A enzyme. Furthermore, partitioning of the increase in catalytic efficiency into the $k_{cat}$ and $K_m$ terms were significantly different (Table VI). These differences probably reflect subtle changes in substrate binding and/or catalytic mechanism between wild-type and the H64A variant enzymes.

TABLE VI

| | Kinetic Analysis of Mutant Subtilisins* against N-succinyl-L-Phe-L-Ala-L-His-L-X-p-nitroanilide where X is Phe or Tyr, at pH 8.60 and (25 ± 0.2)°C. | | | | | | |
|---|---|---|---|---|---|---|---|
| | sFAHF-pna | | | sFAHY-pna | | | P1 |
| Substrate Enzyme | $k_{cat}$ $s^{-1}$ | $K_m$ M | $k_{cat}/K_m$ $s^{-1}M^{-1}$ | $k_{cat}$ $s^{-1}$ | $K_m$ M | $k_{cat}/K_m$ $s^{-1}M^{-1}$ | Preference Tyr/Phe** |
| WT | 4.4 ± 0.5 | 17 ± 2 | $(2.6 \pm 0.2) \times 10^5$ | 5.1 ± 0.1 | 6.6 ± 0.6 | $(7.8 \pm 0.5) \times 10^5$ | 3.0 |
| G166A | 2.3 ± 0.1 | 4.6 ± 0.5 | $(5.1 \pm 0.4) \times 10^5$ | 4.1 ± 0.1 | 26 ± 2 | $(1.6 \pm 0.1) \times 10^5$ | 0.31 |
| E156S: G169A: Y217L | $(5.9 \pm 0.3) \times 10^1$ | 20 ± 3 | $(3.0 \pm 0.3) \times 10^6$ | $(2.8 \pm 0.1) \times 10^1$ | 6.3 ± 0.5 | $(4.4 \pm 0.2) \times 10^6$ | 1.5 |
| E156S: G166A: G169A: Y217L | $(3.8 \pm 0.1) \times 10^1$ | 7.6 ± 0.8 | $(5.0 \pm 0.4) \times 10^6$ | $(3.0 \pm 0.1) \times 10^1$ | 41 ± 4 | $(7.5 \pm 0.6) \times 10^5$ | 0.15 |
| S24C:H64A | $(2.1 \pm 0.1) \times 10^{-2}$ | 340 ± 30 | $(6.2 \pm 0.4) \times 10^1$ | $(9.9 \pm 0.2) \times 10^{-2}$ | 210 ± 10 | $(4.8 \pm 0.1) \times 10^2$ | 7.7 |
| S24C:H64A: G166A | $(3.8 \pm 0.1) \times 10^{-2}$ | 150 ± 10 | $(2.6 \pm 0.1) \times 10^2$ | $(1.5 \pm 0.1) \times 10^{-2}$ | 340 ± 50 | $(4.2 \pm 0.5) \times 10^1$ | 0.16 |
| S24C:H64A: E156S: G169A: Y217L | $(4.5 \pm 0.2) \times 10^{-2}$ | 200 ± 20 | $(2.2 \pm 0.2) \times 10^2$ | $(1.5 \pm 0.1) \times 10^{-1}$ | 150 ± 10 | $(1.0 \pm 0.1) \times 10^3$ | 4.5 |
| S24C:H64A: E156S: G166A: G169A: Y217L | $(8.3 \pm 0.1) \times 10^{-2}$ | 120 ± 10 | $(6.7 \pm 0.2) \times 10^2$ | $(7.9 \pm 0.2) \times 10^{-3}$ | 270 ± 10 | $(2.9 \pm 0.1) \times 10^1$ | 0.043 |

*Mutants are designated by the single letter code for the wild-type amino acid followed by the residue number and then the amino acid replacement. Multiple mutants are identified by listing the single mutant components separated by colons (for example the double mutant Ser24→Cys, His64→Ala is designtated S24C:H64A).
**Calculated from the ratio of $k_{cat}/K_m$ terms for the Tyr P1 and Phe P1 substrate The 4 mutations E156S:G166A:G169A:Y217L together enhance the activity of the wild-type subtilisin with sFAHF-pna by 19-fold. These same mutations increase the activity of the S24C:H64A enzyme with His P2 (sFAHF-pna; Table VI) by 11-fold.

Determination of the substrate specificity of H64A subtilisin BPN' variants is important in assessing their utility in site-specific proteolysis. Specificity determinants for subtilisin extend over at least 6 residues (FIG. 4 ): 4 on the N-terminal side of the scissile bond (P4 through P1) and 2 on the C-terminal side (P1' and P2'). Substrate specificity data for the prototype S24C:H64A variant are summarized in Table VII. A histidine residue at P2 is apparently necessary but not sufficient for efficient polypeptide hydrolysis by S24C:H64A subtilisin BPN'. The P1 residue is also important in determining the efficiency of "substrate-assisted catalysis" by H64A variants, as shown by the qualitatively similar effects of mutants in the P1 pocket upon the activity of wild-type and H64A subtilisin BPN' towards Phe P1 and Tyr P1 substrates (Table VI). However, in addition to Phe P1 and Tyr P1, substrates containing P1 Met and P1 Leu are also expected to be reactive with H64A mutants. Since Phe and Leu are favorable P1 residues for wild-type subtilisin BPN' (Estell, et al., Science 233 (1986) 659–663 ) . In addition to the preference for histidine at P2 and a large hydrophobic residue at P1, all substrates identified to date that are efficiently cleaved by the S24C:H64A enzyme have Phe, Met or Ile at the P4 position. However, it is expected that substrates containing Ala, Leu, Val and Lys as P4 will also be reactive based on the reactivity of wild-type subtilisin with substitutes containing these amino acids at P4. For wild-type subtilisin (and probably for H64A variants) the side chain of the P3 residue is orientated away form the enzyme towards solvent, and consequently there is limited specificity at this sub-site.

TABLE VII

Substrate Specificity of S24C:H64A Variant of Subtilisin BPN'

| P4 | P3 | P2 | P1 | P1' | P2' | Substrate | Reference |
|---|---|---|---|---|---|---|---|
| A. Efficiently Cleaved Substrates | | | | | | | |
| F | A | H | Y | pna | | | Table VI |
| F | A | H | Y | [X]* | G | | Table VIII |
| F | A | H | Y | T | R | Z-AP fusion protein | FIG. 12 and 13 |
| I | N | H | Y | R | M | Inhibin β-chain (residues 61–80) | 1 |
| F | A | H | F | pna | | | Table VI |
| M | E | H | F | R | W | ACTH (residues 1-10) | 1 |
| B. Substrates Not Detectably Cleaved** | | | | | | | |
| T | L | H | L | V | L | Ubiquitin (residues 62-76) | 1 |
| Y | E | H | F | E | N | BOP gene product (residues 68-86) | 1 |
| N | Q | H | L | $C^{SO_3}H$ | G | Bovine Insulin B Chain (Oxidized) | 1 |
| G | S | H | L | V | E | Bovine Insulin B Chain (Oxidized) | 1 |
| R | G | H | S | P | F | Inhibin β-chain (residues 61–80) | 1 |

(*) [X] all common Lα-amino acids except Pro and Ile
(1) Carter, P. and Wells, J. A., Science 237 (1987) 394–399
**Only small peptide substrates where the potential cleavage site is presumably accessible have been included.

TABLE VIII

Digestion of Succinyl-L-Phe-L-Ala-L-His-L Tyr-L-[X]-L-Gly (~0.6 mM) by S24C:H64A Subtilisin BPN' (3.6 μM) at pH 8.0 and (37 ± 0.2)°C.

| P1' residue | Relative No. KCl | Cleaved Rates +2 M KCl |
|---|---|---|
| Pro | <0.1 | ND* |
| Ile | <0.1 | <0.1 |
| Asp | 1 | 14 |
| Glu | 1 | 10 |
| Met | 6 | ND |
| Phe | 7 | ND |
| Leu | 7 | ND |
| Gly | 9 | ND |
| Ser | 10 | 19 |
| Val | 10 | ND |
| Ala | 17 | ND |
| Tyr | 21 | 27 |
| Gln | 23 | 81 |
| Trp | 24 | ND |
| His | 26 | ND |
| Lys | 30 | 45 |
| Thr | 35 | ND |
| Asn | 36 | 58 |
| Cys | 40 | ND |
| Arg | 43** | ND |

*ND, not determined
**This corresponds to an absolute rate of cleavage of $2 \times 10^{-2} s^{-1}$.

The S24C:H64A enzyme has very broad substrate specificity on the C-terminal side of the cleavage site (P1' and P2'). This is desirable since these residues represent the first 2 residues of the protein of interest in a fusion polypeptide. All residues at P1' (apart form Ile and Pro) allow efficient substrate hydrolysis (Table VIII). From proteolysis of protein and synthetic peptide substrates, sequences containing at least Trp, Arg, Met or Gly at P2' can be cleaved efficiently (Table VIIA). It is likely that the Pro P2' is unfavorable for H64A subtilisin as it is for the wild-type enzyme. X-ray crystallography shows that the main-chain amide nitrogen and carbonyl oxygen of the P2' residue make hydrogen bonds with the main-chain carbonyl oxygen and amide nitrogen of Asn218, respectively (Robertus, J. D., et al. (1972), Supra).

The major problem in achieving site-specific proteolysis is that digestion may not be limited to the designed target sequence. Even factor $X_a$ which has a very narrow substrate specificity, occasionally cleaves at other sites besides the Ile-Glu-Gly-Arg target sequence (Nagai, K., et al. (1987), Methods Enzymol., 153, 461–481). Digestion of the Z-AP fusion protein (containing a synthetic IgG binding domain, a target for a cleavage enzyme and E. coli alkaline phosphatase; see Example 12,13) by S24C:H64A subtilisin and the multiple mutant S24C:H64A:E156S:G166A:G169A:Y217L is restricted entirely to the target sequence, even though there are 12 other histidine residues present (Chang, C. N., et al. (1986), Gene, 44, 121–125; Nilsson, B., et al. (1987), Protein Engineering 1, 107–113). Seven of these histidines are surrounded by unfavorable P4, P1 or P1' residues and 4 others are unavailable because the histidine is coordinated to $Zn^{2+}$ in. native AP (Sowadski, J. M., et al. (1985), J. Mol. Biol., 186, 417–433). Aside from the target sequence, only His87 in AP is in the context of a favorable amino acid sequence (Y T $H^{87}Y$ A L). However this site, and all of the other histidine residues present in AP, are at least partially buried in the 3-dimensional structure (Sowadski, J. M., et al. (1985), supra) making them unavailable for hydrolysis. In contrast to S24C:H64A and its variants, the wild-type enzyme rapidly cleaves the Z-AP fusion at 2 sites within 4 residues of the designed target followed by degradation of the AP product. This suggests that the region containing the target is highly accessible.

Assessment of the frequency of naturally occurring sites for S24C:H64A subtilisin rests upon attempting digestion of a large number of protein substrates. Nine other globular proteins (hen egg white lysozyme, horse cytochrome c, horseradish peroxidase, bovine pancreatic ribonuclease, spinach ferredoxin, bovine catalase, bovine serum albumin, human serum albumin and human tissue-type plasminogen activator) which collectively contain more than 80 histidine sites, were not cleaved by the S24C:H64A enzyme under similar (native) conditions as described in Example 12,13 for the digestion of Z-AP fusion protein. In contrast, all of the proteins tested were digested at many sites by wild-type subtilisin. In some cases it may be necessary to denature the fusion protein in order to make the target site accessible for cleavage. Digestion of human serum albumin (contains 16 histidine residues) after reduction and carboxymethylation, gave rise to limited proteolysis by the S24C:H64A enzyme (not shown) at a rate <100-fold that for cleavage of the Z-AP fusion protein.

Based upon the natural abundance of histidine in proteins (2%; Klapper, M. H. (1977) Biochem. Biophys. Res. Commun. 78 1018–1024) and good $P_1$ residues, Tyr, Phe, Leu, and Met (collectively about 22%), the frequency of good cleavage sites that only satisfy the P2 and P1 dominant sequence requirement is ~0.5%. Thus, although other histidines may be present in the product protein, very few are likely to contain satisfactory determinants at P4, P1 and P1' as well as being accessible for hydrolysis by H64A variant subtilisins.

Nevertheless if cleavage does occur at a significant rate at a site additional to the target site then it may be possible to overcome this by judicious choice of enzyme from the H64A family of subtilisin variants and of linker sequence. For example, if the offending site has Tyr P1, then one could use the S24C:H64A:E156S:G166A:G169A:Y217L variant in combination with a Phe P1 linker. This variant favors Phe over Tyr at P1 by 23-fold whilst retaining high catalytic efficiency for Phe P1 (Table VI).

The S24C:H64A subtilisin BPN' variant satisfies most of the criteria considered to be desirable for an ideal site-specific protease. It is exquisitely specific on the N-terminal side of the cleavage site and yet broadly specific on the C-terminal side to allow specific cleavage of a target linker. This enzyme can be recovered free of detectable protease contaminants in high yields (>30 mg/l in shake flasks). It resists a variety of protease inhibitors (including PMSF, EDTA, leupeptin and pepstatin) which permits their use during digestion to inactivate protease contaminants that may be present in fusion protein preparations. This enzyme, like wild-type subtilisin (Wells, J. A., et al. (1986), *J. Biol. Chem.*, 261, 6564–6570), is fully active in reductants or 0.1% (w/v) SDS or 0.1% (v/v) tween 20 and is moderately active in denaturants (20% activity is retained in 2M urea and 10% activity in 2M guanidine hydrochloride against sFAHF-pna, FIG. 11) that may be required to solubilize the fusion protein or to make the target site accessible for cleavage. Activity of the penta-mutant (S24C:H64A:E156S:G169A:Y217L), is enhanced about 4-fold compared with the prototype H64A enzyme with the Z-AP fusion protein, and for both enzymes activity is enhanced ≈3-fold in the presence of 2M KCl and a further 2-fold by performing the digests at 50° C. instead of at 37° C. The penta-mutant has been irreversibly immobilized on a solid support via the C24 residue and retains the ability to cleave the Z-AP fusion, albeit at rates several fold slower than for the free enzyme in solution (see Example 12, 13, 15). This type of protease column eliminates the need to purify the protease away from the cleaved products and facilitates recycling of the protease. A final advantage to a protease which is amenable to rational design such as subtilisin BPN' is that there is an extensive structural and functional data base (Wells, J. A., et al. (1988), *Trends in Biochemical Sciences*, 13, 291–297) that can be utilized as need be for further modification of specificity determinants at the P4, P1, P1' and P2' binding sites.

EXAMPLE 1

Construction of helper subtilisin containing a functionally silent A48E mutation.

The construction of pS4 is described in detail in EPO Publication No. 0130756. This plasmid is depicted in FIG. 6. pS4 contains 4.5 kilobase (kb) of sequence derived from pBS42 (solid line) and 4.4 kb of sequence containing the *B. amyloliquefaciens* subtilisin gene and flanking sequences (dashed line). pBS42 was constructed as described in EPO Publication No. 0130756 and Band, L. and Henner, D. J. (1984) DNA 3, 17–21. It was digested with BamHI and ligated with Sau3A partially digested chromosomal DNA from *B. amyloliquefaciens* (ATCC No. 23844) as described in EPO Publication No. 0120756. pS4 was selected from this genomic library.

pS4-5, a derivative of pS4 made according to Wells, et al. (1983) *Nucleic Acids Res.* 11, 7911–7924, was digested with EcoRI and BamHI, and the 1.5 kb EcoRI-BamHI fragment recovered. This fragment was ligated into replicative form M-13 mp9 which had been digested with EcoRI and BamHI (Sanger, et al., (1980) *J. Mol. Biol.* 143, 161–178; Messing, et al., (1981) *Nucleic Acids Res.* 9, 304–321; Messing, J. and Vieira, J. (1982) *Gene* 19, 269–276). The M-13 mp9 phage ligations, designated M-13 mp9 SUBT, were used to transform *E. coli* strain JM101 (ATCC 33876) and single stranded phage DNA was prepared from a two mL overnight culture. An oligonucleotide primer was synthesized having the sequence

5'-GTAGCAGGCGGAGAATCCATGGTTCC-3

The primer included the sequence of the subtilisin gene fragment encoding amino acids 44 through 52 except that the codon 48 normally encoding alanine was substituted with the codon GAA encoding glutamate; the serine codon at 49 (AGC) was also converted to TCC to introduce a convenient NcoI site.

The primer (about 15 μM) was labelled with [$^{32}$P] by incubation with [$\gamma^{32}$p]-ATP (10 μL in 20 μL reaction) (Amersham 5000 Ci/mmol, 10218) and T$_4$ polynucleotide kinase (10 units) followed by non-radioactive ATP (100 μM) to allow complete phosphorylation of the mutagenesis primer. The kinase was inactivated by heating the phosphorylation mixture to 68° C. for 15 minutes.

The primer was hybridized to M-13 mp9 SUBT as modified from Norris, et al., (1983) *Nucleic Acids Res.* 11, 5103–5112 by combining 5 μL of the labelled mutagenesis primer (~3 μM), ~1 μg M-13 mp9 SUBT template, 1 μL of 1 μM M-13 sequencing primer (17-mer), and 2.5 μL of buffer (~0.3M Tris pH 8, 40 mM MgCl$_2$, 12 mM EDTA, 10 mM DTT, 0.5 mg/ml BSA). The mixture was heated to 68° C. for 10 minutes and cooled 10 minutes at room temperature. To the annealing mixture was added 3.6 μL of 0.25 mM dGTP, dCTP, dATP, and dTTP, 1.25 μL of 10 mM ATP, 1 μL ligase (4 units) and 1 μL Klenow (5 units). The primer extension and ligation reaction (total volume 25 μL) proceeded 2 hours at 14° C. The Klenow and ligase were inactivated by heating to 68° C. for 20 minutes. The heated reaction mixture was digested with BamH1 and EcoRI and an aliquot of the digest was applied to a 6 percent polyacrylamide gel and radioactive fragments were visualized by autoradiography. This showed the [$^{32}$P] mutagenesis primer had indeed been incorporated into the EcoRI-BamH1 fragment containing the now mutated subtilisin gene.

The remainder of the digested reaction mixture was diluted to 200 μL with 10 mM Tris, pH 8, containing 1 mM EDTA, extracted once with a 1:1 (v:v) phenol/chloroform mixture, then once with chloroform, and the aqueous phase recovered. 15 μL of 5M ammonium acetate (pH 8) was added along with two volumes of ethanol to precipitate the DNA from the aqueous phase. The DNA was pelleted by centrifugation for five minutes in a microfuge and the supernatant was discarded.

300 μL of 70 percent ethanol was added to wash the DNA pellet, the wash was discarded and the pellet lyophilized.

pBS42 was digested with BamH1 and EcoRI and purified on an acrylamide gel to recover the vector. 0.5 μg of the digested vector, 0.1 μg of the above primer mutated EcoRI-BamHI digested subtilisin genomic fragment, 50 μM ATP and 6 units ligase were dissolved in 20 μl of ligation buffer. The ligation went overnight at 14° C. The DNA was transformed into the *B. subtilis* host BG2036.

EXAMPLE 2

Construction of H64A Mutant Subtilisin

The *B. amyloliguifaciens* subtilisin gene on a 1.5 kb EcoRI-BamHI fragment (Wells, J. A., et al., (1983) *Nucleic Acids Res.* 11, 7911-7925) was cloned into M13mpll (Messing, J. and Vieira, J., (1982) *Gene* 19, 269-276) to give M13mp11SUBT and single-stranded DNA was isolated (Carter, P., et al., (1985) in "Oligonucleotide site-directed mutagenesis in M13" Anglian Biotechnology Limited). The mutation H64A was constructed using the synthetic oligonucleotide H64A \* \* \* \*
(5' CAACAACT<u>CCGCGG</u>GAACTCAC 3')

and the M13SUBT template using a previously described method (Carter, P., et al., (1985) *Nucleic Acids Res.* 13, 4431-4443). The asterisks in HA64 denote mismatches to the wild-type sequence and the underlined is a unique SacII restriction site.

The primer (H64A) was annealed to the single-stranded M13SUBT template extended for 12 hrs. at 4° C. with DNA polymerase I (Klenow fragment) in the presence of deoxynucleoside triphosphates and T4 DNA ligase (Carter, P., et al., (1985) *Nucleic Acids Res.* 13, 4431-4443). The M13 heteroduplex DNA was then transfected directly into the *E. coli* host BMH 71-18 mutL (Kramer, B., et al., (1984) *Cell* 38, 879-887). Mutant phage were identified by colony blot hybridization screening as previously described (Carter, P. J., et al., (1984) *Cell* 38, 835-840).

Putative H64A mutants were verified by dideoxy nucleotide sequencing (Sanger, F., et al., (1977) *Proc. Natl. Acad. Sci. USA* 77, 5463-5467) as modified by Bankier, A. T. and Barrell, B. G., (1983) in "Techniques in the life sciences " B5,*Nucleic Acids Biochemistry*, B508, 1, Elsevier, Ireland and designated M13mpllSUBT-Ala-64. The 1.5 kb EcoRI-BamHI fragment from M13mpllSUBT-Ala-64 was isolated and ligated with the 3.7 kb EcoRI-BamHI fragment from the *B. subtilis—E. coli* shuttle vector pBS42 (Band, L. and Henner, D. J., (1984) *DNA* 3, 17-21). *E. coli* MM294 cells (Murray, N. E., et al., (1977) *Mol. Gen. Genet.* 150, 53) were transformed with the ligation mixture using a CaCl₂ procedure (Cohen, S. N., Chang, A. C. Y., and Hsu, L., (1972) *Proc. Natl. Acad. Sci. USA* 69, 2110-2114). Plasmid DNA was recovered from individual transformants using an alkaline-sodium dodecyl sulfate (SDS) procedure (Birboim, H. C. and Doly, J., (1979) *Nucleic Acids Res.* 7, 1513-1528 as modified by Burke, J. F. and Ish-Horowicz, D., (1982) *Nucleic Acids Res.* 10, 3821-3830) to generate pBS42SUBT-Ala-64. The H64A mutation was verified by restriction endonuclease digests of the plasmid DNA using the enzymes SacII and BamHI which generate a 0.9 kb fragment.

EXAMPLE 3

Construction of the double mutant S24C:H64A

The double mutant S24C:H64A was constructed from the single mutants pBS42SUBT-Cys-24 (Wells, J. A. and Powers, D. B., (1986) *J. Biol. Chem.* 261, 6564-6570) and pBS42SUBT-Ala-64 (this document) by a 3-way ligation using the following fragments: 3.7 kb EcoRI/BamHI from pBS42, 0.5 kb EcoRI/ClaI from pBS42SUBT-Cys-24 and the 1.0 kb ClaI/BamHI from pBS42SUBT-Ala-64. The double mutant Cys-24/Ala-64 was identified by restriction endonuclease site markers introduced by the single mutations (His-64->Ala: new SacII site; Ser-24->Ala: Sau3A site removed) and designated pBS42SUBT-Cys-24/Ala-64. The pBS42SUBT-Cys-24/Ala-64 plasmid was introduced into the *B. subtilis* host BG2036 (Anagostopoluos, C. and Spizizen, J., (1961) *J. Bacteriol.* 81, 741-746) deficient in alkaline and neutral proteases (Yang, M. Y., et al., (1984) *J. Bacteriol.* 160, 15-21).

EXAMPLE 4

Expression of S24C:H64A subtilisin BPN' by Co-culturing with A48E subtilisin BPN' or by culturing in the presence of purified wild-type subtilisin BPN'

Mutant subtilisin genes were expressed in BG2036 by fermentation in shake flasks using 2×TY media (Miller, J. H., (1972) in "Experiments in Molecular Genetics ", Cold Spring Harbor Laboratory, Cold Spring Harbor, N.Y.) containing 12.5 μg/ml chloramphenicol at 37° C. for 18-20 hrs. Co-cultures were made by diluting S24C:H64A cultures 1:100 and A48E cultures 1:100,000 in 2×TY containing 12.5 μg/ml chloramphenicol and grown at 37° C. for 20-24 hrs with vigorous aeration.

An alternative procedure is to omit the co-culturing step above and to include purified wild-type subtilisin BPN' enzyme or the A48E enzyme, or some other active subtilisin mutant enzyme in the culturing step. A suitable amount of active subtilisin is 1 mg/l of the culture.

EXAMPLE 5

Purification of S24C:H64A

Cultures were centrifuged (8,000g, 15 min., 4° C.) and 3 volumes of ethanol (−20° C.) added to the supernatant. After centrifugation (8,000g, 15 min., 4° C.), the pellet was resuspended in 50 mM Tris.HCl (pH 8.0), 5mM CaCl₂, 10 mM dithiothrietol (DTT), 0.1 mM phenylmethylsulfonyl fluoride (PMSF). After centrifugation (40,000 g, 30 min., 4° C.) the supernatant was dialyzed against 2 l 10mM 2-[N-morpholino]ethanesulfonic acid (MES) (pH 6.0), 5 mM CaCl₂, 10 mM DTT, 0.1 mM PMSF (S buffer) overnight at 4° C. The dialysate was passed over a 50 ml DE52 (Whatman) column and loaded on to 50 ml CM Trisacryl (LKB) column. Subtilisin was eluted with a 600 ml gradient of S buffer containing 0-100 mM NaCl at 1.5 ml/min. Pooled subtilisin containing fractions were dialyzed against 2 L deaerated 10 mM MES (pH 6.0), 5 mM CaCl₂, 100 mM NaCl, 0.1 mM PMSF (T buffer). Samples were loaded on to an activated thiol sepharose matrix (Pharmacia) washed extensively with T buffer and then eluted with T buffer containing 20 mM DTT. The eluate was concentrated using Centricon 10 microconcentrators (Amicon) and then transferred to 10 mM MES (pH 6.0), 5 mM CaCl₂, 10 mM DTT, 0.1 mM PMSF (U buffer) by gel filtration using PD10 G25 (Pharmacia) columns. The concentration of subtilisin was determined from the measured absorbance at 280 nm ($E_{280}$ 0.1%=1.17) (Matsubara, H., et al., (1965) *J. Biol. Chem.* 240, 1125–1130). Aliquots of purified enzyme were flash frozen in liquid nitrogen and then stored at −70° C.

EXAMPLE 6

Preparative native gel electrophoresis 1.5mg S24C:H64A subtilisin in U buffer (defined in Example 5) was adjusted to 10 mM phenyl boronate, 10% glycerol (v/v) and 0.1% (w/v) methylene blue. The sample was electrophoresed for 24 hrs. at 7 W (constant) on a 10% polyacrylamide gel (20 cm×20 cm×0.75 cm) with recirculating buffer. The running buffer and gel contained 10 mM phenyl boronate, 2 mM $CaCl_2$, 5 mM DTT 50 mM histidine and 60 mM 3-[N-morpholino]propanesulfonic acid (MOPS). The protein was diffusion-blotted on to nitrocellulose (Hancock, K., and Tsang, V. C. W., (1983 *Anal. Biochem.* 133, 157–162 as modified by Carter, P., et al., (1986) *Proc. Natl. Acad. Sci. USA* 83, 1189–1192). Subtilisin was visualized after binding rabbit anti-subtilisin antibody (Power, S. D., et al., (1986) *Proc. Natl. Acad. Sci. USA* 83, 3096–3100) then horse radish peroxidase conjugated protein A by using the chromogenic substrate 3,3'-diaminobenzidine tetrahydrochloride. Subtilisin containing gel slices were placed in dialysis bags with 6 ml running buffer (omitting phenyl boronate) and electroeluted at 10mA (constant) for 20 hrs. at 4° C. Recovered material was concentrated and transferred to U buffer as for column purified enzyme (above).

EXAMPLE 7

Kinetic analysis of S24C:H64A

The kinetic parameters for S24C and S24C:H64A were determined against the substrates N-succinyl-L-Phe-L-Ala-L-[X]-L-Phe-p-nitroanilide (abbreviated sFAXF-pna), where X (P2 position) was Ala, Gln, or His (Table IX). The kinetic parameters for the S24C enzyme are essentially identical to wild-type subtilisin against these substrates indicating that the S24C mutation is kinetically silent. By comparison, the H64A mutation causes a drop of $10^6$ fold in $k_{cat}/K_m$ against the Ala and Gln P2 substrates. Almost all of the decrease in catalytic efficiency is caused by a decreased $k_{cat}$ term (up to $10^6$ times), although smaller but significant increases appear in $K_m$. Unlike wild-type or S24C subtilisin, the S24C:H64A enzyme was completely resistant to inhibition by the active site reagent, phenylmethylsulfonyl-fluoride (PMSF). This suggests the catalytic histidine is critical for stable sulfonylation by PMSF. Although the proportion of functional active sites in S24C:H64A enzyme preparations could not be determined directly by such active site labeling, enzyme that was purified by additional native gel electrophoresis (Example 6) had identical kinetic parameters to S24C:H64A described in Table IX.

The data are consistent with His-64 being extremely important in catalysis (presumably by proton transfer) and only marginally important in substrate binding. However, because we cannot be sure that acylation is rate limiting for the H64A mutant, as it is for the wild-type enzyme (Wells, J. A. (1986) *Phil. Trans. R. Soc. Lond. A*, 317, 415–423), the relatively small changes in $K_m$ may not reflect changes in the enzyme-substrate dissociation constant ($K_s$) but rather a shift in the rate determining step of the reaction (Guttreund, et al. (1956) *Biochem J.*, 63, 656). In any case, removal of the catalytic imidazole causes a reduction of about $10^6$-fold in the total enzymatic rate enhancement (Table IX).

The catalytic efficiency ($k_{cat}/K_m$) of S24C toward the three P2 substrates are all within a factor of five of each other. For the S24C:H64A mutant, $k_{cat}/K_m$ for the Ala and Gln P2 substrates are essentially the same; however, hydrolysis of the HisP2 substrate is 170 to 210 times more efficient, respectively. Essentially all of the increase in $k_{cat}/K_m$ for the His over the Ala and Gln P2 substrates results from the $k_{cat}$ term being larger by a factor of 2,000 and 500, respectively. The larger $K_m$ values for the His and Gln P2 substrates compared to Ala may reflect reduced binding affinity resulting from a bulky group at P2. Larger $K_m$ values are also observed for the Gln and His substrates for the S24C enzyme. Thus, the drop in $k_{cat}/K_m$ caused by the H64A mutation is partially restored when cleaving a His P2 substrate. The net effect is a marked increase in substrate preference for a His P2 side-chain brought about at the level of catalysis rather than binding. The nonenzymatic hydrolysis rate of the HisP2 substrate is similar to the Ala and Gln P2 substrates (Table IX). Thus, the His P2 substrate only becomes functionally active in the context of the catalytic groups provided by the enzyme.

The fact that the catalytic efficiency of the S24C:H64A mutant against the His P2 substrate is 5,000 fold below wild-type suggests the His from the substrate P2 functions poorly in catalysis. This may result from the His P2 making poor steric contacts and/or improper alignment of the catalytic triad. Indeed, the model of the His P2 side-chain does not exactly match the catalytic His-64 in that the planes of the histidines from the enzyme and substrate are almost perpendicular to each other (FIG. 5).

EXAMPLE 8 pH Dependence of Amide Bond Hydrolysis by S24C:H64A Subtilisin

The pH dependence of $k_{cat}/K_m$ for wild-type subtilisin shows a sigmoidal increase from pH 6 to 8 (Glazer, A. N. (1967), *J. Biochem.*, 242 433) that reflects the titration of the catalytic His64 ($pK_a = 7.1 \pm 0.1$). The wild-type pH profile remains relatively flat over the range of 8–10 and declines thereafter (Ottesen, et al. (1970), *In Methods of Enzymology* (Ed. Perleman, Acad. Press, N.Y., Vol 19, p. 199)).

FIG. 7 shows the pH dependence of hydrolysis of p-nitroanilide peptide substrates by S24C:H64A subtilisin. Analysis of S24C:H64A against sFAAF-pna (FIG. 7A) was determined as in Table IX except using 100 mM Tris.HCl or 100 mM 3-[cyclohexylamino]-1-propane sulfonic acid (CAPS) buffer. The data was fitted assuming a linear relationship with hydroxide ion concentration (solid lines in FIGS. 7A and 7B). Analysis of S24C:H64A with sFAHF-pna (FIG. 7C) was determined as in Table IX except using 100 mM 3-[N-morpholino] propanesulfonic acid (MOPS) buffer (filled circles) or 100 mM Tris.HCl (open circles) and then normalizing the ionic strength using KCl. The data was fitted to a sigmoid relationship (solid line) using a least-squares fit procedure.

The pH dependence of $k_{cat}/K_m$ is markedly different for the S24C:H64A enzyme. For the sFAAF-pna substrate, there is an increase of 15 fold in the $k_{cat}/K_m$ between pH 8 to 10 (FIG. 7A). $k_{cat}/K_m$ shows a linear dependence upon hydroxide ion concentration (FIG. 7B) suggesting that a hydroxide ion can act as a catalytic base in the absence of a catalytic histidine side chain. If one were to extrapolate from the increase in $k_{cat}/K_m$ as a function of hydroxide concentration ($2\times10^4$ s$^{-1}$M$^{-2}$), to the $k_{cat}/K_m$ for S24C against this same Ala P2 substrate ($8\times10^5$ s$^{-1}$M$^{-1}$), then the equivalent concentration of the hydroxide ion would be about 40M.

In contrast, the $k_{cat}/K_m$ for hydrolysis of the sFAHF-pna by S24C:H64A shows a sigmoidal pH dependence between pH 6 and 8 (FIG. 7C) that is similar to wild-type subtilisin. The p$K_a$ of the activity dependent group is 6.8±0.1, and almost all of the pH dependent changes in $k_{cat}/K_m$ result from changes in $k_{cat}$ (data not shown). For the sFAHF-pna substrate, there is not a strong linear increase in $k_{cat}/K_m$ with hydroxide above pH 8 as observed for hydrolysis of sFAAF-pna. These data strongly suggest that the P2 histidine side-chain from the substrate can substitute functionally for the missing catalytic histidine 64.

The data presented in Table IX (measured at pH 8.6) underestimate the substrate preference for His over Ala (and Gln) because the $k_{cat}/K_m$ for the sFAHF-pna is maximal at pH 8.0 (FIG. 7C), whereas for the sFAAF-pna substrate it is significantly lower at pH 8.0 (FIG. 7B). Thus, for S24C:H64A at pH 8.0, we estimate the substrate preference is up to 400 times for the His P2 substrate over the corresponding Ala or Gln substrates.

TABLE IX

Kinetic analysis of mutant subtilisin against the substrates, N-succinyl-L-Phe-L-Ala-L-X-L-Phe-$p$-nitroanilide, where X is Ala, Gln, or His. Six hydrolysis assays were performed simultaneously against corresponding substrate blanks in 0.10M Tris-HCl (pH 8.6), 10 mM DTT at 25±0.1° C. using a Kontron unvikon 860 spectrophotometer. Initial reaction rates were determined from the increase in absorbance caused by the release of $p$-nitroaniline ($\epsilon_M^{410}$=8,480M$^{-1}$, cm$^{-1}$ (Del-Mar, E. G., et al. (1979) Anal. Biochem. 99 316)) and fitted by linear regression to an Eadie-Hofstee plot to calculate V$_{max}$ and K$_m$. $k_{cat}$ was calculated from V$_{max}$/[enzyme], using the spectrophotometrically determined enzyme concentration (Matsubara, et al. (1965) J. Biol. Chem. 240, 1125). Enzyme concentrations in the assays were about 50 μg/mL for S24C:H64A and 1 μg/mL for S24C. Standard errors in all determinations were below 20%. Slight variation in the absolute kinetic values has been observed between batches of enzyme, but the relative values among substrates has remained constant.

differences in the energetics of substrate binding and/or catalysis. Thirdly, the mutant is completely resistant to inhibition by PMSF, unlike other serine proteases. In fact, the kinetic determinations for the S24C:H64A mutant are routinely made in the presence of PMSF to exclude any possibility of active "helper" subtilisin (Table IX, FIG. 7). Fourthly, the substrate dependent pH profiles are unlike any protease we are aware of. Fifthly, preparations of S24C:H64A are extremely pure from other contaminating proteins based by analysis on SDS and native gels (>99%). Finally, the kinetic values determined for S24C:H64A that was additionally purified by native gel electrophoresis (Example 6) are essentially the same as these reported in Table IX.

EXAMPLE 9

Hydrolysis of Polypeptide Substrates by S24C:H64A Subtilisin

To further evaluate the specificity of the S24C:H64A mutant in comparison with S24C, both enzymes were incubated with a 20 residue fragment of the inhibin β chain at pH 8.0 (Carter, P. and Wells, J. A., Science (1987) 237 394–399). The choice of the peptide was based upon the presence of two histidines (position 5 and 11) along with 16 different amino acids, and a variety of large hydrophobic amino acids that are preferred amino acids at the P1 position of wild-type subtilisin (Estell, D. A., et al. (1986) Science 233, 659). FIG. 8 shows the hydrolysis of the inhibin peptide substrate TVINHY↓RMRGHSPFANKLSC by S24C:H64A subtilisin. This substrate (100 μg) was digested with 10μg S24C:H64A (FIG. 8A) or 0.13 μg S24C (FIG. 8B). Reaction mixtures were in a total volume of 250 μL containing 20 mM Tris.HCl (pH 8.0), 10 mM dithiothreitol, 5% (v/v) dimethyl sulfoxide and 1 mM PMSF (S24C:H64A only). After indicated times at 37° C., digestion products (monitored at 214 nm) were eluted from a reverse phase HPLC column (Waters, C18) using a gradient (from left to right) of 0–50% (v/v) acetonitrile in 0.1% (v/v) trifluoroacetic acid.

After a 2-hour incubation with S24C:H64A (FIG. 8A), a ~120 fold molar excess of inhibin peptide (peak a) was cleaved to greater than 95% completion into two pieces (peaks b and c). Amino acid composition analysis of these two peptide fragments indicated cleavage had occurred between Tyr-6 and Arg-7, as expected for substrate assisted catalysis by His-5 located at the P2 position from cleavage site. After 10-fold longer digestion (20 hr.) a minor third peak appeared (labelled X in FIG. 8A). Analysis showed it to have the same composition as the undigested inhibin peptide. This minor product also appeared in a non-enzymatic blank incubation. No digestion was observed at the second histidine site.

|  | S24C | | | S24C:H64A | | | Non-enzymatic |
|---|---|---|---|---|---|---|---|
| Substrate P2 residue | $k_{cat}$ s$^{-1}$ | $K_m$ μM | $k_{cat}/K_m$ s$^{-1}$M$^{-1}$ | $k_{cat}$ s$^{-1}$ | $K_m$ μM | $k_{cat}/K_m$ s$^{-1}$M$^{-1}$ | hydrolysis rate (s$^{-1}$) |
| Ala | 8.1 | 10 | 8.0 × 10$^5$ | 8.1 × 10$^{-6}$ | 32 | 0.25 | 1.7 × 10$^{-7}$ |
| Gln | 7.0 | 39 | 1.8 × 10$^5$ | 3.0 × 10$^{-5}$ | 150 | 0.20 | 7.1 × 10$^{-8}$ |
| His | 4.6 | 23 | 2.0 × 10$^5$ | 1.6 × 10$^{-2}$ | 380 | 42 | 7.9 × 10$^{-8}$ |

Several lines of evidence indicate that the activity we attribute to the S24C:H64A enzyme is not the result of any other protease contamination. Firstly, the extreme substrate preference for His at the P2 position is unlike wild-type subtilisin or any known Bacillus protease. Secondly, the mutant has $K_m$ values which are significantly different from wild-type subtilisin suggesting In contrast to the two fragments produced by S24C:H64A the S24C enzyme produced at least seven fragments (FIG. 8B) at a similar extent of digestion of starting material (compare 5 min. digestion with S24C to 2 hr. digestion with S24C:H64A). Although none of these seven fragments were sequenced, the first two produced eluted from the HPLC profile at the same positions as peaks b and c in FIG. 8A. Digestion to 95% completion of the starting peptide by S24C (30 min. incubation, FIG. 8C) produced more than ten different peptide fragments.

EXAMPLE 10

Construction of Mutants of S24C:H64A Subtilisin

The mutations S24C:H64A:E156S:G169A:Y217L in the cloned *Bacillus amyloliquefaciens* gene (Wells, J. A., et al. (1983), *Nucl. Acids Res.*, 11, 7911–7925) were constructed by ligating 3 fragments: 0.75 kb EcoRI/PvuI from pBS42SUBT-Cys-24/Ala-64 (Example 3) 0.75 kb PvuI/BamHI from the plasmid encoding E156S:G169A:Y217L (Wells, J. A., et al. (1987), *Proc. Natl. Acad. Sci.*, 84, 5167–5171; EPO Publication No. 035,652). The mutants S24C:H64A:G166A and S24C:H64A:E156S:G166A:G169A:Y217L were constructed by site-directed mutagenesis (Carter, P., et al. (1985), *Nucleic Acids Res.*, 13, 4431–4443) using a 36-mer oligonucleotide

(5' GGTACCTCCGG CTCGAGCACAGTGGCCTACCCT 3' where * indicates mismatches and underline a new XhoI site) to install the G166A mutation. The templates used were M13mpllSUBT-Cys-24/Ala-64 and M13mpllSUBT-Cys-24/Ala-64/Ser-156/Ala-169/Leu-217 which are constructed from corresponding mutant subtilisin genes in the vector pBS42 (described above) in a manner analogous to Example 2. (The G166A mutation is introduced as previously described in Wells, et al. (1987), supra and EPO Publication No. 035,652.) Putative S24C:H64A:G166A and S24C:H64A:E156S:G166A:G169A:Y217L mutants in M13 were verified and then recloned into the vector pBS42 in a manner analogous to Example 2 and designated pBS42SUBT-Cys-24/Ala-64/Ala-166 and pBS42SUBT-Cys-24/Ala-64/Ser-156/Ala-166/Ala-169/Leu-217, respectively. These mutants were transformed into the *B. Subtilis* host BG2036 as described in Example 3 and then expressed and purified as described in Examples 4 and 5.

EXAMPLE 11

Analysis of S24C:H64A Subtilisin and Mutants Thereof

Mutant enzymes were assayed with substrates, N-succinyl-L-Phe-L-Ala-L-His-L-X-p-nitroanilide, where X is either Phe or Tyr (sFAHF-pna and sFAHY-pna, respectively), against corresponding blanks in 1 ml 100 mM Tris-HCl at pH 8.60, 4% (v/v) dimethyl sulfoxide (Me$_2$SO) at (25±0.2)°C. with a Kontron Uvikon 860 spectrophotometer. Initial reaction rates were determined from the increase in absorbance at 410 nm on release of p-nitroaniline ($\epsilon_{410}$=8,480 M$^{-1}$ cm$^{-1}$; Del Mar, E. G., et al (1979) *Anal. Biochem.* 99, 316–320) and fitted to the Michaelis-Menten equation using a least-squares fit procedure (Carter, P., et al. (1988) *Nature* 332, 564–568). Enzyme concentrations (determined spectrophotometrically; $\epsilon_{Z80}^{0.1\%}$=1.17, Matsubara, H., et al. (1965) *J. Biol. Chem.* 240, 1125–1130) in the assays were 1–20 nM for H64 containing enzymes and 0.3–2 μM for H64A containing enzymes. The substrate concentrations were determined after total hydrolysis and corrected for background hydrolysis and were in the range of 0.1 $K_m$ to 10 times $K_m$.

The S24C:H64A enzyme (1.9 μM) was assayed with the substrate sFAHF-pna (200 μM) as described above (except that the concentration of Me$_2$SO was 1% (v/v)) in the presence of varying amounts of KCl, NaCl, guanidine hydrochloride, urea, SDS, sodium deoxycholate, nonidet P-40 or tween 20.

Peptide substrates (~0.6 mM) having the form N-succinyl-L-Phe-L-Ala-L-His-L-Tyr-L-[X]-L-Gly (where [X] represents the 20 common amino acids) were digested by S24C:H64A subtilisin (3.6 mM) in 1 ml 20 mM Tris.HCl at pH 8.0, 1 mM dithiothreitol (DTT), 0.1 mM phenylmethylsulfonyl fluoride (PMSF), 3.5% (v/v) Me$_2$SO, in the presence or absence of 2M KCl at 37° C. At various times digests were applied to a C18 reverse phase HPLC column (Waters) and eluted with a gradient of 0 to 40% (v/v) acetonitrile in 0.1% (v/v) trifluoroacetic acid. Elution of the substrate and N-succinyl-L-Phe-L-Ala-L-His-L-Tyr product fragment were monitored at 280 nm and quantified by peak integration and amino acid composition analysis. The relative (and absolute) cleavage rate for each peptide substrate was estimated from the initial rate of product formation in 4–6 successive time points.

EXAMPLE 12

Construction, Expression, Purification and Digestion of Z-AP Fusion Protein

A phagemid pZAP encoding the Z-AP fusion protein was constructed by ligating 3 fragments: 4.4-kilobase HindIII (filled-in)-NarI from protein A phagemid vector pEZ (Nilsson, B., et al. (1987), *Protein Engineering*, 1, 107–113), 1.4-kilobase NotI (filled-in)-MluI from the *E. coli* alkaline phosphatase (AP) gene (Chang, C. N., et al. (1986), *Gene*, 44, 121–125) engineered with sites for MluI and NotI (3' to coding sequence) and a synthetic cassette coding for a histidine-containing linker with MluI and NarI compatible ends. See FIG. 12. The ligation mixture was transformed into *E. coli* JM101 and plated on to LB plates containing the chromogenic substrate for AP (5-bromo-4-chloro-3-indolyl phosphate; 2 mg/ml). Several AP expressing clones (blue colonies) were verified by dideoxy sequence analysis (Sanger, F., et al. (1977), *Proc. Natl. Acad. Sci. USA*, 74, 5463–5467).

The Z-AP fusion was expressed in *E. coli* JM101 containing pZAP, purified from osmotically shocked cells by binding to IgG sepharose, and eluted with lithium diiodosalicylate Nilsson, B., et al. (1985), *EMBO J.*, 4, 1075–1080). The purified Z-AP fusion protein was desalted by gel filtration (PD10 disposable columns, Pharmacia) and then dialyzed at 4° C. overnight against 2 liters 50 mM Tris.HCl at pH 8.0. Aliquots were flash frozen and stored at −70° C. Samples of the Z-AP fusion protein that were digested by mutant subtilisins (as described for FIG. 13), were precipitated with 10% (w/v) trichloroacetic acid and analyzed by SDS-PAGE (Laemmli, U. K. (1970), *Nature*, 227, 680–685). The AP digestion product ($M_r$=47,000) was electroblotted on to polyvinylidene difluoride membrane (Matsudaira, P. (1987), *J. Biol. Chem.*, 262, 10035–10038) and the N-terminus was sequenced directly.

EXAMPLE 13

Effect of Subtilisin Mutants on Catalytic Efficiency

A. Enhancing the Catalytic Efficiency of Subtilisin

The mutations G166A (Estell, D. A., et al. (1986), *Science*, 233, 659–663) and E156S:G169A:Y217L (Wells, J. A., et al. (1987), *Proc. Natl. Acad. Sci. USA*, 84, 5167–5171) Which enhance the activity of wild-type subtilisin BPN' towards N-succinyl-L-Ala-L-Ala-L-Pro-L-Phe-p-nitroanilide (sAAPF-pna), were examined first singly and then in combination using the substrate sFAHF-pna (Table VI, supra). The catalytic efficiency, $k_{cat}/K_m$, of wild-type subtilisin with sFAHF-pna was increased 2 and 12-fold by the mutations G166A and E156S:G169A:Y217L, respectively, and by 19-fold by combining these enhanced activity mutants.

Wild-type subtilisin hydrolyses the Tyr P1 substrate sAAPY-pna more efficiently than the homologous Phe P1 substrate (sAAPF-pna) (Estell, D. A., et al. (1986), *Science*, 233, 659–663). Accordingly, both the wild-type and the E156:G169A:Y217L enzymes showed increases in $k_{cat}/K_m$ towards sFAHY-pna compared to sFAHF-pna. As expected, the G166A enzyme, which has been previously shown to sterically exclude a sAAPY-pna substrate (Estell, D. A., et al. (1986), supra), is similarly reduced on the sFAHY-pna substrate. This was also found for the mutant E156S:G166A:G169A:Y217L.

The combined effects of these binding site mutants were then evaluated in the context of the H64A mutation with Phe P1 and Tyr P1 substrates (Table VI). A surface accessible thiol (S24C) that has no effect upon enzyme activity (Carter, P., et al. (1987), *Science*, 237, 394–399), was introduced into all H64A variant subtilisins to facilitate their purification. Numerous control studies (Carter, P., et al. (1987), supra; Carter, P., et al. (1988), *Nature*, 332, 564–568) have demonstrated that the purified active site mutants are free of detectable contaminating protease activity. The G166A variant or the combination of the 3 mutations (E156S:G169A:Y217L) improved $k_{cat}/K_m$ by about 4-fold each. When all 4 mutations were introduced into the S24C:H64A enzyme, $k_{cat}/K_m$ was increased by more than 11-fold. The results with the Tyr P1 substrate toward the S24C:H64A family of enzymes parallel also those with the wild-type family; the S24C:H64A:E156S:G169A:Y217L variant was the most efficient catalyst followed by the S24C:H64A enzyme. Variants containing the G166A mutation were actually much worse due to steric hindrance for the Tyr P1 substrate as expected. Thus, the best enzyme-substrate pair within this family is the penta-mutant (S24C:H64A:E156S:G169A:Y217L) subtilisin with the sFAHY-pna substrate; this enzyme is nearly 20-fold improved over the prototype pair (S24C:H64A hydrolyzing the sFAHF-pna substrate).

Be Survey of Conditions for Hydrolysis Assay for S24C:H64A Subtilisin

The prototype S24C:H64A enzyme was assayed under a variety of conditions to assess their use in digestion of protein substrates (FIG. 11). High concentrations of salt enhance the activity of the S24C:H64A enzyme (FIG. 11A), as has been shown for the wild-type enzyme (Otteson, M., et al. (1970), *Compt. Rend. Tray. Lab. Carlsberg*, 38, 369–383). The S24C:H64A variant retains 50% of its activity in the presence of 1M urea or 0.5M guanidine hydrochloride (FIG. 11B). The S24C:H64A variant is active in non-ionic (tween 20 and nonidet P-40) and ionic (SDS and sodium deoxycholate) detergents and at concentrations that are frequently used to solubilize and denature most proteins (e.g., 0.1% (w/v) SDS). There was no detectable loss of activity during the kinetic runs (up to 30 min) under any of these conditions.

C. P1' Specificity of S24C:H64A Subtilisin

Specificity determinants for subtilisin BPN' extend for 2 residues on the C-terminal side of the scissile bond (P1' and P2', FIG. 10), which represent the first 2 residues of the protein of interest in a fusion protein. The P1'specificity of the S24C:H64A enzyme was studied using the family of peptide substrates: N-succinyl-L-Phe-L-Ala-L-His-L-Tyr-L[X]-L-Gly, where X represents the 20 common amino acids (Table VI, supra). The Phe-Ala-His-Tyr sequence was chosen as the most favorable p-nitroanilide substrate that we have identified for S24C:H64A subtilisin; glycine at P2' was chosen to minimally satisfy the P2'-enzyme main chain interactions. The relative rates of peptide cleavage were measured by the rate of formation of the product N-succinyl-L-Phe-L-Ala-L-His-L-Tyr (Table VIII). In every case hydrolysis occurred exclusively after the Tyr residue as expected. All of the P1' substrates were hydrolyzed at rates within 7-fold of each other except for those containing Asp or Glu, which were cleaved slowly, or Pro or Ile which were not cleaved at detectable rates. Hydrolysis of Asp or Glu P1' substrates was stimulated 10-fold by addition of 2M KCl and cleavage of other substrates tested was increased 1.5 to 3.5-fold.

D. Specific Cleavage of a Model Fusion Protein

A model fusion protein was constructed (FIG. 12) that contains one synthetic (Z) domain of *Staphylococcus aureus* protein A (Nilsson, B., et al. (1987), *Protein engineering*, 1, 107–113), followed by the optimized histidine-containing linker (Phe-Ala-His-Tyr) and *E. coli* alkaline phosphatase (AP). See Example 12. In an attempt to improve the accessibility of the site for cleavage, the target linker was preceded by the sequence Pro-Gly, where the glycine replaces a trypsin-sensitive lysine in protein A (Sjödahl, J. (1977), *Eur. J. Biochem.*, 78, 471–490). Furthermore, the N-terminus of AP is susceptible to proteolysis by both trypsin (Roberts, C. H., et al. (1984), *J. Biol. Chem.*, 259, 729–733) (between Arg11 and Ala12) and by V8 protease (Tyler-Cross, R., et al. (1989), *J. Biolo Chem.*, 264, 4523–4528) (between Glu9 and Asn10). AP was also an attractive marker protein because a similar fusion protein was expressed in high yield in the periplasmic space of *E. coli* with very little proteolytic degradation (Nilsson, B., et al. (1985), *EMBO J.*, 4, 1075–1080) and AP can be readily assayed using chromogenic substrates. The fusion protein was designed so that cleavage at the target site generates AP with an additional N-terminal Thr residue. This sequence (containing a Mlu I site) was particularly convenient to construct, and simplifies any subsequent manipulations to substitute the P1'residue. The protein A derived fusion protein was efficiently purified by IgG affinity chromatography as previously described (Nilsson, B., et al. (1985), supra).

Protease digestion experiments (FIG. 13) show that the prototype enzyme (S24C:H64A) and the most active penta-mutant variant (S24C:H64A:E156S:G169A:Y217L) cleave the fusion protein ($M_r=54,000$) efficiently and specifically to generate a protein with the expected electrophoretic mobility of AP ($M_r=47,000$). The protein A fragment ($M_r=7,000$) is too small to be resolved from the dye-front on this gel. N-terminal sequence analysis of the purified AP product in each case gave the sequence expected for cleavage at the designed target site (Thr-Arg-Thr-Pro-Glu-Met-Pro). Digestion by the penta-mutant was about 4-fold faster than by the prototype H64A variant, and in each case the cleavage rate was enhanced about 3-fold by 2M KCl as was observed for many of the peptide substrates (Table VIII).

EXAMPLE 14

Cleavage of Z-bIGF-I Fusion Protein by S24C:H64A:E156S:G169A:Y217L Subtilisin (bIGF-I=brain insulin-like growth factor one)

A phagemid pZbIFG-I encoding the Z-bIGF-I fusion protein was constructed in a manner analogous to that for pZAP (Example 12) by ligating 3 fragments: 4.4-kilobase HindIII (filled-in)-NarI from protein A phagemid vector pEZ (Nilsson, B., et al. (1987), supra, 0.25-kilobase NotI (filled-in)-MluI from bIGF-I engineered with sites for MluI and NotI (3' to coding sequence) and a synthetic cassette (exactly as in FIG. 12) coding for a histidine-containing linker with MluI and NarI compatible ends. See FIG. 14. The ligation mixture is transformed into *E. coli* JM101 and several clones are verified by dideoxy sequence analysis (Sanger, F., et al. (1977), *Proc. Natl. Acad. Sci. USA*, 74, 5463–5467). The Arg residue at the 2nd position of bIGF-I (introduced when the MluI site was installed) is converted back to the natural residue (leucine) by site-directed mutagenesis (Carter, P. 1985 supra).

The Z-bIGF-I fusion protein was expressed in *E. coli* JM101 containing pZbIGF-I, purified from osmotically shocked cells by binding to IgG sepharose, and eluted with 1M acetic acid.

Aliquots of Z-bIGF-I were lyophilized, resuspended in distilled water and re-lyophilized. After resuspending in distilled water, aliquots were flash frozen and stored at −70° C. The Z-bIGF-I fusion protein was digested with S24C:H64A:E156S:G169A:Y217L subtilisin BPN' under the same conditions as used for the Z-AP fusion protein (Examples 12, 13 and as described for FIG. 13). The digestion products were analyzed by reverse phase HPLC as described in Example 9. Collected peaks were lyophilized and analyzed by mass spectroscopy (FIG. 15). The observed mass/charge (m/z) ratio (7366.4) for bIGF-I isolated after cleavage of Z-bIGF-I was in excellent agreement with the theoretical value (7366.41). Furthermore Z-bIGF-I was very efficiently cleaved by the S24C:H64A:E156S:G169A:Y217L subtilisin BPN' variant without having to reduce the 3 disulfide bridges present in the b-IGF-I molecule.

EXAMPLE 15

Activity of S24C:H64A:E156S:G169A:Y217L Subtilisin BPN' After Immobilization on a Solid Support The penta-mutant subtilisin variant S24C:H64A:E156S:G169A:Y217L was immobilized on to thiopropyl-sepharose 6B (Pharmacia) (the same solid support as used in Example 5) as follows:

1) The S24C:H64A:E156S:G169A:Y217L enzyme (60 nmol) was activated at the Cys24 thiol with 1.5 μmol N,N'-1,4-phenylenedimaleimide in the presence of 100 mM Tris-HCl (pH 7.5), 5 mM CaCl₂, for 1 hr at 4° C. Excess cross-linking reagent was then removed by gel filtration.

2) The thiopropyl-sepharose 6B resin was deprotected by washing with 20 mM DTT in 100 mM Tris HCl (pH 8.0), and then equilibrated with 100 mM Tris-HCl (pH 7.5), 5 mM CaCl₂.

3) The deprotected thiopropyl-sepharose 6B resin was then mixed gently with the activated enzyme from (1) above (overnight, 4° C.). The resin was equilibrated with 100 mM Tris-HCl (pH 8.0), and then remaining free thiol groups on the support blocked with 100 mM iodoacetamide in 100 mM Tris HCl (pH 8.0) (2 hr, 4° C.). Finally, the resin was washed extensively with 100 mM Tris-HCl (pH 7.5), 5 mM CaCl₂.

4) The loading of enzyme on the resin was estimated from the known amount of S24C:H64A:E156S:G169A:Y217L enzyme (60 nmol) used for coupling and that which remained in solution after the coupling step (estimated from the enzyme activity).

Immobilized S24C:H64A:E156S:G169A:Y217L subtilisin BPN' was found to cleave the Z-AP fusion protein, albeit a few-fold slower than in solution. Immobilization of subtilisin BPN' via Cys-24 provides a unique and defined attachment point to a solid support. Furthermore, Cys-24 is located on the surface of the enzyme distant from the active site (FIG. 16). Thus immobilization of subtilisin BPN' via Cys-24 should not compromise the accessibility of the active site of the enzyme even to macromolecular substrates such as proteins.

The immobilization of enzymes has been extensively described in the literature (see Methods in *Enzymology*, 135, 136, 137).

Furthermore, numerous immobilized proteases are commercially available, including the following taken from the 1989 Catalogue of the Sigma Chemical Company: subtilisin BPN', bovine trypsin and α-chymotrypsin, carboxypeptidase A, papain, pepsin, proteinase K, thermolysin, *Streptomyces griseus* protease, and *Staphylococcus aureus* V8 protease.

These immobilized proteases are highly active even against macromolecular substrates. Indeed the activity units used by Sigma are usually based upon hydrolysis of the milk protein, casein.

EXAMPLE 16

Stimulation of the Activity of S24C:H64A Subtilisin BPN' by Imidazole

The S24C:H64A variant of subtilisin BPN' and also the wild-type enzyme, were assayed with the substrate N-succingl-L-Ala-L-Ala-L-pro-L-phe-p-nitroanilide (sAAPFpna) in 1 ml 100 mM Tris-HCl (pH 8.60) 4% (v/v) dimethyl sulfoxide at 25±0.2° C. with a Kontron Uvikon spectrophotometer, by the method of initial rates as described by Carter, P., et al. (1988), *Nature*, 332, 564–568, except that the assays included varying concentrations of imidazole and the ionic strength was kept constant by adjusting with NaCl. For the S24C:H64A enzyme $k_{cat}$ with sAAPFpna was increased in the presence of imidazole (Table XI) reaching a maximal 4-fold enhancement in the presence of 300 mM imidazole.

$K_m$ also increased with increasing imidazole so that at high imidazole concentrations $k_{cat}/K_m$ actually decreased slightly. In contrast to the S24C:H64A variant, $k_{cat}$ for the wild-type enzyme with sAAPF-pna was relatively unaffected by imidazole concentrations up to 900 mM (Table X). $K_m$ for the wild-type enzyme increased almost 10-fold in the presence of 900 mM imidazole (Table X).

Thus, hydrolysis of the non-histidine substrate (sAAPF-pna) by S24C:H64A subtilisin can be stimulated by the addition of an exogenous general base, in this case imidazole.

TABLE X

Kinetic Analysis of wild-type subtilisin BPN' against sAAPF-pna at pH 8.60 and (25 ± 0.2)°C. in the presence of varying concentrations of imidazole.

| [Imidazole] mM | $k_{cat}$ $s^{-1}$ | $K_m$ mM | $k_{cat}/K_m \times 10^5 \, s^{-1}M^{-1}$ |
|---|---|---|---|
| 909 | 66.1 ± 1.4 | 2.0 ± 0.1 | 0.33 ± 0.1 |
| 795 | 65.4 ± 1.0 | 1.5 ± 0.1 | 0.44 ± 0.01 |
| 682 | 71.4 ± 1.2 | 1.3 ± 0.1 | 0.56 ± 0.01 |
| 568 | 65.2 ± .19 | 0.95 ± 0.08 | 0.69 ± 0.01 |
| 455 | 72.4 ± 2.3 | 0.74 ± 0.06 | 0.98 ± 0.1 |
| 318 | 64.3 ± 1.2 | 0.54 ± 0.03 | 1.2 ± 0.1 |
| 182 | 65.1 ± 1.0 | 0.39 ± 0.02 | 1.7 ± 0.1 |
| 0 | 57.6 ± 0.7 | 0.21 ± 0.01 | 2.8 ± 0.1 |

TABLE XI

Kinetic Analysis of S24C:H64A variant of subtilisin BPN' against sAAPF-pna at pH 8.60 and (25 ± 0.2)°C. in the presence of varying concentrations of imidazole.

| [Imidazole] mM | $k_{cat} \times 10^{-4} \, s^{-1}$ | $K_m$ mM | $k_{cat}/K_m$ $s^{-1}M^{-1}$ |
|---|---|---|---|
| 909 | 2.8 ± 0.1 | 8.9 ± 0.7 | 3.1 ± 0.2 |
| 454 | 2.8 ± 0.1 | 4.2 ± 0.3 | 6.6 ± 0.4 |
| 318 | 2.8 ± 0.1 | 3.3 ± 0.3 | 8.9 ± 0.6 |
| 200 | 2.0 ± 0.1 | 3.1 ± 0.3 | 6.6 ± 0.5 |
| 100 | 1.5 ± 0.1 | 1.9 ± 0.2 | 7.8 ± 0.8 |
| 50 | 1.2 ± 0.2 | 2.5 ± 0.3 | 4.5 ± 0.2 |
| 0 | 0.65 ± 0.03 | 1.8 ± 0.2 | 3.6 ± 0.3 |

The effect of imidazole on hydrolysis of the nonhistidine containing substrate sFAAF-pna by S24C:H64A subtilisin BPN' was investigated exactly as described for the sAAPF-pna substrate above.

FIG. 17 depicts the imidazole dependence of hydrolysis of sFAAF-pna at pH 8.60 and (25±0.2)° C. by S24C:H64A subtilisin BPN'.

$k_{cat}$ for sFAAF-pna with the S24C:H64A enzyme was increased ~20-fold in the presence of 750 imidazole (FIG. 17) and $K_m$ was increased ~10-fold.

Thus the function of a missing catalytic group (in this case, histidine) can be restored at least partially by supplying an equivalent functional moiety (in this case, the imidazole moiety) exogenously.

Having described the preferred embodiments of the present invention, it will appear to those ordinarily skilled in the art that various modifications may be made to the disclosed embodiments and that such modifications are intended to be within the scope of the present invention.

All literature references are expressly incorporated herein by reference.

What is claimed is:

1. A catalytically active enzyme-substrate complex comprising a subtilisin-related protease variant in contact with a first substrate containing a first selected region, wherein said variant is not found in nature and is formed by the replacement or modification of a catalytic histidine in a precursor subtilisin-related protease with an amino acid having a side-chain volume less than the side chain volume of histidine, said catalytic histidine being functional with a second selected region of a second substrate, wherein said subtilisin-related protease variant is substantially less active catalytically with said second substrate as compared to said first substrate and wherein said first selected region comprises said second selected region wherein one of the residues has been substituted with histidine.

2. The enzyme-substrate complex of claim 1 wherein said subtilisin-related protease comprises subtilisin.

3. The enzyme-substrate complex of claim 2 wherein said first substrate contains a target cleavage sequence reactive with said variant comprising in order amino acid residues P4, P3, P2, P1 and P1', where said P2 amino acid residue is histidine and said first substrate is capable of being cleaved by said variant at the peptide bond between said P1 and P1' residues.

4. The enzyme-substrate complex of claim 3 wherein said P1 residue is selected from the group consisting of tyrosine, phenylalanine, methionine, leucine and lysine.

5. The enzyme-substrate complex of claim 4 wherein said P1 residue is tyrosine.

6. The enzyme-substrate complex of claim 3 wherein said P1 residue is phenylanine.

7. The enzyme-substrate complex of claim 3 wherein said P4 residue is selected from the group consisting of phenylalanine, isoleucine, methionine, alanine, leucine, sysine and valine.

8. The enzyme-substrate complex of claim 7 wherein said P4 residue is phenylalanine.

9. The enzyme-substrate complex of claim 2 wherein said subtilisin comprises B. amyloliquefaciens subtilisin and said catalytic histidine comprises His-64.

10. The enzyme-substrate complex of claim 9 wherein said first substrate contains a target cleavage sequence comprising the amino acid sequence phenylalanine-alanine-histidine-tyrosine.

11. The enzyme-substrate complex of claim 9 wherein said modified substrate contains a target cleavage sequence comprising the amino acid sequence phenylalanine-alanine-histidine-phenylalanine.

12. The enzyme-substrate complex of claim 9 wherein said His-64 is replaced by Ala.

* * * * *